United States Patent
Schense et al.

(10) Patent No.: US 10,589,001 B2
(45) Date of Patent: Mar. 17, 2020

(54) PHARMACEUTICAL FORMULATION FOR USE IN SPINAL FUSION

(75) Inventors: Jason Schense, Zürich (CH); Silke Mark, Brugg (CH); Monica Alvisi, Zürich (CH); Maria Angeles Martinez Vargas, Zürich (CH)

(73) Assignee: Kuros Biosurgery AG, Zurich (CH)

(*) Notice: Subject to any disclaimer, the term of this patent is extended or adjusted under 35 U.S.C. 154(b) by 939 days.

(21) Appl. No.: 13/226,618

(22) Filed: Sep. 7, 2011

(65) Prior Publication Data

US 2012/0234718 A1 Sep. 20, 2012

Related U.S. Application Data

(63) Continuation of application No. PCT/EP2011/054008, filed on Mar. 16, 2011.

(51) Int. Cl.
| | | |
|---|---|---|
| A61F 2/00 | (2006.01) | |
| A61L 27/12 | (2006.01) | |
| A61L 27/54 | (2006.01) | |
| A61L 27/22 | (2006.01) | |
| A61L 27/46 | (2006.01) | |

(52) U.S. Cl.
CPC ............ *A61L 27/12* (2013.01); *A61L 27/225* (2013.01); *A61L 27/227* (2013.01); *A61L 27/46* (2013.01); *A61L 27/54* (2013.01); *A61L 2300/414* (2013.01); *A61L 2300/43* (2013.01); *A61L 2400/06* (2013.01); *A61L 2430/38* (2013.01)

(58) Field of Classification Search
CPC ......... A61F 2/44; A61F 2/442; A61K 9/0019; A61K 9/0024; A61K 38/00; A61K 38/29; A61L 27/225; A61L 27/54; C07K 14/635
See application file for complete search history.

(56) References Cited

U.S. PATENT DOCUMENTS

| | | |
|---|---|---|
| 4,086,196 A | 4/1978 | Tregear |
| 4,590,760 A | 5/1986 | Goebel |
| 4,613,665 A | 9/1986 | Larm |
| 4,663,931 A | 5/1987 | Schiffers |
| 4,810,784 A | 3/1989 | Larm |
| 4,917,702 A | 4/1990 | Scheicher |
| 5,069,905 A | 12/1991 | Lidor |
| 5,100,668 A | 3/1992 | Edelman |
| 5,171,670 A | 12/1992 | Kronenberg |
| 5,202,247 A | 4/1993 | Kilburn |
| 5,428,014 A | 6/1995 | Labroo |
| 5,504,001 A | 4/1996 | Foster |
| 5,510,370 A | 4/1996 | Hock |
| 5,529,986 A | 6/1996 | Larsson |
| 5,561,982 A | 10/1996 | Tunkel |
| 5,582,862 A | 12/1996 | Reed |
| 5,641,670 A | 6/1997 | Tunkel |
| 5,693,341 A | 12/1997 | Schroeder |
| 5,747,456 A | 5/1998 | Chorev |
| 5,773,577 A | 5/1998 | Capello |
| 5,814,603 A | 9/1998 | Oldenburg |
| 5,840,837 A | 11/1998 | Krstenansky |
| 5,874,308 A | 2/1999 | Kilburn |
| 5,874,500 A | 2/1999 | Rhee |
| 5,877,153 A | 3/1999 | Harris |
| 5,958,874 A | 9/1999 | Clark |
| 6,026,957 A | 2/2000 | Bauer et al. |
| 6,054,122 A | 4/2000 | MacPhee |
| 6,117,425 A | 9/2000 | MacPhee |
| 6,136,564 A | 10/2000 | Kopetzki |
| 6,197,325 B1 | 3/2001 | MacPhee |
| 6,206,957 B1 | 3/2001 | Driessens |
| 6,221,854 B1 | 4/2001 | Radomsky |
| 6,303,138 B1 | 10/2001 | Peterson |

(Continued)

FOREIGN PATENT DOCUMENTS

| | | |
|---|---|---|
| DE | 20010297 | 8/2000 |
| EP | 725145 | 8/1996 |

(Continued)

OTHER PUBLICATIONS

Lane JM, SV Bukata, E Tomin, B Shore, and M Cunningham. 2005. PTH(1-34) stimulates Spine Fusion. Poster Abstracts: Osteoporosis Treatment. The Sixth International Symposium on Osteoporosis: Current and Future Directions [online]; downloaded from <http://nof.confex.com/nof/2005/techprogram/P132.htm> on Jul. 9, 2012; 1 page.*

Zdeblick TA and FM Phillips. Interbody cage devices. Spine (Phila Pa 1976). 2003; 28(15): abstract.*

Takagi, et al., "Amino acid sequence studies on the alpha chain of human fibrinogen. Location of four plasmin attack points and a covalent cross-linking site," Biochemistry 14 (23):5149-56 (1975).

Adams, et al., "Roles of ephrinB ligands and EphB receptors in cardiovascular development: demarcation of arterial/venous domains, vascular morphogenesis, and sprouting angiogenesis," Genes & Development 13:295-306 (1999).

(Continued)

*Primary Examiner* — David Browe
(74) *Attorney, Agent, or Firm* — Pabst Patent Group LLP

(57) ABSTRACT

A pharmaceutical formulation for use in a spinal fusion method, comprising a composition for forming a matrix, a kit comprising the composition, a pharmaceutical product obtainable from the pharmaceutical formulation, and an interbody spinal fusion cage containing the pharmaceutical formulation or the pharmaceutical product are described herein. The composition comprises at least a first matrix material precursor component and a second matrix material precursor component that are able to crosslink to form the matrix under appropriate conditions, a bioactive factor that is biologically active for stimulating bone formation between two vertebrae and for effecting or supporting spinal fusion. The bioactive factor is PTH, optionally a PTH fusion peptide. The bioactive factor is releasably incorporated in the matrix upon crosslinking of the matrix material precursor components.

14 Claims, 2 Drawing Sheets
Specification includes a Sequence Listing.

(56) References Cited

U.S. PATENT DOCUMENTS

| | | |
|---|---|---|
| 6,331,422 B1 | 12/2001 | Hubbell |
| 6,372,257 B1 | 4/2002 | Marchosky |
| 6,468,543 B1 | 10/2002 | Gilbertson |
| 6,468,731 B1 | 10/2002 | Hubbell |
| 6,541,022 B1 | 4/2003 | Murphy |
| 6,559,119 B1 | 5/2003 | Burgess |
| 6,607,740 B1 | 8/2003 | Hubbell |
| 6,608,293 B2 | 8/2003 | Kuderer |
| 6,663,870 B2 | 12/2003 | Hart |
| 6,730,721 B2 | 5/2004 | Bezemer |
| 6,894,022 B1 | 5/2005 | Hubbell |
| 6,960,452 B2 | 11/2005 | Hubbell |
| 7,026,292 B1 | 4/2006 | Lee |
| 7,045,105 B2 | 5/2006 | Lagow |
| 7,052,856 B2 | 5/2006 | Ting |
| 7,229,826 B2 | 6/2007 | Kale |
| 7,241,730 B2 | 7/2007 | Hubbell |
| 7,247,609 B2 | 7/2007 | Lutolf |
| 7,601,685 B2 | 10/2009 | Hubbell |
| 2003/0012818 A1 | 1/2003 | Schense |
| 2003/0103957 A1 | 6/2003 | McKerracher |
| 2003/0166833 A1 | 9/2003 | Lutolf |
| 2003/0180376 A1 | 9/2003 | Dalal |
| 2003/0187232 A1 | 10/2003 | Hubbell |
| 2004/0082513 A1 | 4/2004 | Hubbell |
| 2005/0010297 A1 | 1/2005 | Watson |
| 2005/0065281 A1 | 3/2005 | Lutolf |
| 2005/0163817 A1 | 7/2005 | Masters |
| 2005/0175665 A1 | 8/2005 | Hunter |
| 2006/0147443 A1 | 7/2006 | Schense |
| 2006/0148704 A1* | 7/2006 | Schense et al. ............... 514/12 |
| 2006/0168718 A1 | 8/2006 | Watson |
| 2007/0010440 A1 | 1/2007 | Schense |
| 2007/0017903 A1 | 1/2007 | Change |
| 2007/0202178 A1 | 8/2007 | Schense |
| 2007/0254011 A1 | 11/2007 | Schnabelrauch |
| 2007/0264227 A1 | 11/2007 | Lutolf |
| 2009/0010940 A1 | 1/2009 | Morley et al. |
| 2011/0311643 A1* | 12/2011 | Schense et al. ............ 424/602 |

FOREIGN PATENT DOCUMENTS

| | | |
|---|---|---|
| EP | 950665 | 10/1999 |
| EP | 1604693 | 12/2005 |
| FR | 2552443 | 3/1985 |
| WO | 8900051 | 1/1989 |
| WO | 9005177 | 5/1990 |
| WO | 9202620 | 2/1992 |
| WO | 9209301 | 6/1992 |
| WO | 9222312 | 12/1992 |
| WO | 9420133 | 9/1994 |
| WO | 9505396 | 2/1995 |
| WO | 9523611 | 9/1995 |
| WO | 9531423 | 11/1995 |
| WO | 9617633 | 6/1996 |
| WO | 9931137 | 6/1999 |
| WO | 0010596 | 3/2000 |
| WO | 0044808 | 8/2000 |
| WO | 0064481 | 11/2000 |
| WO | WO 01/48148 | 7/2001 |
| WO | 0176558 | 10/2001 |
| WO | 02085422 | 10/2002 |
| WO | 03040235 | 5/2003 |
| WO | 03052091 | 6/2003 |
| WO | WO 03/070186 | 8/2003 |
| WO | 04071543 | 8/2004 |
| WO | WO 06/067221 | 6/2006 |
| WO | 2006072622 | 7/2006 |
| WO | 2006072623 | 7/2006 |
| WO | WO 06/072622 | 7/2006 |
| WO | WO 06/072623 | 7/2006 |
| WO | WO 08/064132 | 5/2008 |
| WO | WO 09/105723 | 8/2009 |
| WO | WO 09/120433 | 10/2009 |
| WO | WO 10/048610 | 4/2010 |

OTHER PUBLICATIONS

Baumgartner, et al, "Constitutive expression of phVEGF165 after intramuscular gene transfer promotes collateral vessel development in patients with critical limb ischemia," Circulation, 97:1114-1123 (1998).

Besson, et al., "Synthetic peptide substrates for a conductimetric assay of Pseudomonas aeruginosa elastase," Analytical Biochemistry 237(0232):216-223 (1996).

Blaess, et al., "Structural analysis of the sixth immunoglobulin-I Ike domain of mouse neural cell adhesion molecule L1 and Its interactions with alpha v beta 3, aphallb beta3 and apha 5 beta1 integrins," J Neurochem 71:2615-2625 (1998).

Boden, "Overview of the Biology of Lumbar Spine Fusion and Principles for Selecting a Bone Graft Substitute" , Spine, 27(165):S26-S31 (2002).

Bonadio, et al., "Localized, direct plasmid gene delivery in vivo: prolonged therapy results in reproducible tissue regeneration" Nat Med., 5(7):753-9 (1999).

Borrajo, et al., "Derivatized Cyclodextrins as peptidometics: Influence on Neurite Growth," Bioorganic and Medicinal Chemistry Letters, 7:1185-90 (1997).

Brooks, et al., "Requirement of vascular integrin alphavbeta3 for angiogenesis," Science, 264:569-571 (1994).

Bruckner, "EphrinB ligands recruit GRIP family PDZ adaptor proteins into raft membrane microdomains," Neuron 22:511-524 (1999).

Calderwood, et al., "Integrins and actin filaments: reciprocal regulation of cell adhesion and signaling," J Biol Chem, 275:22607-22610 (2000).

Camarata, et al., "Sustained Release of Nerve Growth Factor from Biodegradable Polymer Microspheres," Neurosurgery 30(3) 313-319 (1992).

Cardin, et al., "Molecular Modeling of Protein-Glycosaminoglycan Interactions," Arterioscler Thromb Vasc Biol, 9:21-32 (1989).

Carr et al., "Effects of ionic and nonionic contrast media on clot structure, platelet function and thrombolysis mediated by tissue plasminogen activator in plasma clots" ,Haemostasis, 25(4):172-81 (1995).

Conover, et al., "Disruption of Eph/ephrin signaling affects migration and proliferation in the adult subventricular zone," Nature Neuroscience 3 (11):1091-3324 (2000).

Coombs, et al., "Directing sequence-specific proteolysis to new targets. The influence of loop size and target sequence on selective proteolysis by tissue-type plasminogen activator and urokinase-type plasminogen activator", J. Biol. Chem., 273(8):4323-4328 (1998).

Coussons, et al. "Factors that govern the specificity of transglutaminase-catalysed modification of proteins and peptides" Biochemical L., 282:929-30 (1992).

Dalva, et al., "EphB receptors interact with NMDA receptors and regulate excitatory synapse formulation," Cell, 103:945-956 (2000).

Deblois, et al., "Heparin-fibroblast growth factor-fibrin complex: in vitro and in vivo applications to collagen-based materials" , Biomaterials., 15(9):665-72 (1994).

Dedhar and Hannigan, "Integrin cytoplasmic interactions and bidirectional transmembrane signaling," Current Opinion in Cell Biology, 8:657-669 (1996).

Dempster, et al., "Anabolic actions of parathyroid hormone on bone", Endocrine Rev., 14:690-709 (1993).

Dimilla, et al., "Mathematical model for the effects of adhesion and mechanics on cell migration speed," Biophys. J. 60(1):15-37 (1991).

Dinbergs, et al., "Cellular response to transforming growth factor-beta1 and basic fibroblast growth factor depends on release kinetics and extracellular matrix interactions," J. Biol. Chem., 271(47):29822-9 (1996).

Downs, et al., "Calcium Alginate Beads as a Slow-Release System for Delivering Angiogenic Molecules in Vivo and In Vitro," Journal of Cellular Physiology 152:422-429 (1992).

Edelman, et al., "Basic fibroblast growth factor enhances the coupling of intimal hyperplasia and proliferation of vasa vasorum in injured rat arteries," J. Clin. Invest., 89 (2):465-73 (1992).

(56) References Cited

OTHER PUBLICATIONS

Edelman, et al., "Controlled and modulated release of basic fibroblast growth factor," Biomaterials. 12(7):619-26 (1991).
Edelman, et al., "Perivascular and intravenous administration of basic fibroblast growth factor: vascular and solid organ deposition," Proc. Natl. Acad. Sci. U. S. A., 90(4):1513-7 (1993).
Edgar, et al., "The heparin-binding domain of laminin is responsible for its effects on neurite outgrowth and neuronal survival," EMBO J. 3(7):1463-8 (1984).
Eliceiri and Cheresh, "The role of v integrins during angiogenesis: insights into potential mechanisms of action and clinical development," Journal of Clinical Investigation, 103:1227-1230 (1999).
Epstein, "Pros, cons, and costs of INFUSE in spinal surgery", Surgical Neurology International, 2:10 (2011).
Esposito and Caputo, "Mammalian transglutaminases. Identification of substrates as a key to physiological function and physiopathological relevance", FEBS J., 272(3):615-31 (2005).
Fasol, et al., "Experimental use of a modified fibrin glue to induce site-directed angiogenesis from the aorta to the heart," Journal of Thoracic and Cardiovascular Surgery, 107:1432-9 (1994).
Felding-Habermann, et al., "A single immunoglobulin-like domain of the human neural cell adhesion molecule L1 supports adhesion by multiple and platelet integrins," J Cell Biol, 139:1567-1581 (1997).
Feng, et al., "Roles for ephrins in positionally selective synaptogenesis between motor neurons and muscle fibers," Neuron, 25:295-306 (2000).
Ferrara, "Molecular and biological properties of vascular endothelial growth factor," J Mol Med, 77:527-543 (1999).
Ferrara and Alitalo, "Clinical applications of angiogenic growth factors and their inhibitors," Nature Medicine, 5:1359-1364 (1999).
Folkman, "Angiogenesis in cancer, vascular, rheumatoid and other disease," Nature Medicine 1:27-31 (1995).
Gabriel, et al., "The effect of fibrin structure in fibrinolysus", J. Biol. Chem., 267 (3):24259-63 (1992).
Gale, et al., "Ephrin-B2 selectivity marks arterial vessels and neovascularization sites in the adult, with expression in both endothelial and smooth-muscle cells," Developmental Biology, 230:151-160 (2001).
Gehrig, et al., "Osteoporosis: Management and treatment strategies of orthopedic surgeons", J Bone and Joint Surg., 90:1362-74 (2008).
Gerasimov, et al., "The Role of lysosomes in the pathogenesis of unicameral bone cysts", Clinical Orthopedics and Related Res., 266:53-63 (1991).
Giannelli, et al., "Transforming growth factor-beta1 triggers hepatocellular carcinoma invasiveness via alpha3beta1 integrin", Am J Pathol., 161(1):183-93 (2002).
Gittens, et al. "Designing Proteins for Bone Targeting", Advanced Drug Delivery Reviews 57(7):1-11-1036(2005).
Grainger, et al., "Poly(dimethylsiloxane)-poly(ethylene oxide)-heparin block copolymers. I. Synthesis and Characterization," J. Biomed. Mater Res., 22(3):231-249 (1988).
Grant, et al., "Mapping the structural properties of the lumbosacral vertebral endplates", Spine, 26(8):889-896 (2001).
Griesler, et al., "Enhanced endothelial of expanded polyethrafluoroethylene grafts by fibroblast growth factor type 1 pretreatment," Surgery 112:244-255 (1992).
Groenen, et al., "The carboxy-terminal lysine of alpha B-crystallin is an amine-donor substrate for tissue transglutaminase", Eur J Biochem., 205(2):671-4 (1992).
Grootjans, et al., "Substrate requirements for transglutaminases. Influence of the amino acid residue preceding the amine donor lysine in a native protein", J Biol Chem., 270(39):22855-8 (1995).
Götz, et al., "Neurotrophin-6 is a new member of the nerve growth factor family," Nature 372(6503):266-9 (1994).
Hall, et al., "Trimerization of cell adhesion molecule L1 mimics clustered L1 expression on the cell surface: Influence on L1-Ligand interactions and on promotion of neurite outgrowth," J of Neurochemistry, 75:336-346 (2000).
Hall, "Molecular properties of fibrin-based matrices for promotion of angiogenesis in vitro," Microvascular Research, 62:315-326 (2001).
Hammoud, et al., "Management of coronary artery disease: Therapeutic options in patients with diabetes," J Am. Col. Cardiology, 36:355-65 (2000).
Harada, et al., "Basic fibroblast growth factor improves myocardial function in chronically ischemic porcine hearts," J. Clin. Invest., 94(2):623-30 (1994).
Hata, et al., "Binding of lipoprotein lipase to heparin. Identification of five critical residues in two distinct segments of the amino-terminal domain," J. Biol. Chem. 268(12):8447-57 (1993).
Haugen, et al, "Central and peripheral neurite outgrowth differs in preference for heparin-binding versus integrin-binding sequences," J. Neurosci., 12(6):2034-42 (1992).
Herbert, et al., "Effects of fibinolysis on neurite growth from dorsal root ganglia cultured in two- and three-dimensional fibrin gels," J. Comp. Neurol. 365(3):380-91 (1996).
Herbert, et al., "Effects of fibrin micromorphology on neurite growth fro m dorsal root ganglia cultured in three-dimensional fibrin gels," J. Biomed. Mat. Res., 40(4):551-9 (1998).
Hern and Hubbell, "Incorporation of adhesion peptides into non-adhesive hydrogels useful for tissue resurfacing", J. Biomed. Mater. Res., 39:266-276 (1998).
Houle & Johnson, "Nerve growth factor (NGF)-treated nitrocellulose enhances and directs the regeneration of adult rat dorsal root axons through intraspinal neural tissue transplants," Neuroscience Letters, 103:17-23 (1989).
Hsu, et al., "Comparing ectopic bone growth induced by rhBMP-2 on an absorbable collagen sponge in rat and rabbit models", Journal of orthopaedic research, 24(8):1660-69 (2006).
Hubbell, "Bioactive biomaterials" Curr. Opinion Biotechnol. 10(2):123-129 (1999).
Humphries, "Integrin activation: the link between ligand binding and signal transduction," Curr Opin Cell Biol, 8:632-640 (1996).
Ilan, et al., "Distinct signal transduction pathways are utilized during the tube formation and survival phases of in vitro angiogenesis," J of Cell Science 111:3621-3631 (1998).
Ingber and Folkman, "How does extracellular matrix control capillary morphogenesis?" Cell, 58:803-805 (1989).
Jagur-Grodzinski, et al. "Biomedical application of functional polymers", Reactive Polymers 39(2):99-138(1999).
Jeong, et al., "The fibronectin-binding domain of transglutaminase", J Biol Chem., 270(10):5654-8 91995).
Kallapur, et al, "The neural cell adhesion molecule (NCAM) heparin binding domain binds to cell surface heparan sulfate proteoglycans," J. Neuro. Res. 33(4):538-48 (1992).
Kandziora, et al., "Bioabsorbable interbody cages in a sheep cervical spine fusion model", Spine, 29(17):1845-55 (2004).
Kandziora, et al., "Comparison between sheep and human cervical spines: an anatomic, radiographic, bone mineral density, and biomechanical study", Spine, 26(9):1028-37 (2001).
Kaneda, et al., "Midkine, a heparin-binding growth/differentiation factor, exhibits nerve cell adhesion and guidance activity for neurite outgrowth in vitro," J. Biochem. 119(6):1150-6 (1996).
Kang, et al., "Selective stimulation of endothelial cell proliferation with inhibition of smooth muscle cell proliferation by fibroblast growth factor-1 plus heparin delivered from glue suspensions," Surgery, 118:280-287 (1995).
Kiguchi, et al., "Altered expression of epidermal growth factor receptor ligands in tumor promoter-treated mouse epidermis and in primary mouse skin tumors induced by an initiation-promotion protocol," Mol. Carcinog. 22(2):73-83 (1998).
Kinosaki, et al., "Identification of heparin-binding stretches of a naturally occurring deleted variant of hepatocyte growth factor (dHGF)," Biochim. Biophys. Acta., 1384(1):93-102 (1998).
Kleinman, et al., "The laminins: a family of basement membrane glycoproteins important in cell differentiation and tumor metastases," Vitam. Horm.47:161-86 (1993).
Lee, et al., "Analysis of affinity and structural selectivity in the binding of proteins to glycosaminoglycans: Development of a sensitive electrophoretic approach," Biochemistry, 88:2768-2772 (1991).

(56) References Cited

OTHER PUBLICATIONS

Lin, et al., "Purification and Initial Characterization of Rat B49 Glial Cell Line-Derived Neurotrophic Factor," Journal of Neurochemistry 758-768 (1994).
Lopez, et al., "Basic fibroblast growth factor in a porcine model of chronic myocardial ischemia: a comparison of angiographic, echocardiographic and coronary flow parameters," J. Pharmacol. Exp. Ther. 282(1):385-90 (1997).
Lopez, et al., "Local perivascular administration of basic fibroblast growth factor: drug delivery and toxicological evaluation," Drug Metab. Dispos. 24(8):922-4 (1996).
Lorsordo, et al., "Gene therapy for myocardial angiogenesis. Initial clinical results with direct myocardial injection of phVEGF165 as sole therapy for myocardial ischemia," Circulation 98:2800-2804 (1998).
Ludbrook, et al., "The integrin alphavbeta3 is a receptor for the latency-associated peptides of transforming growth factors beta1 and beta3", Biochem. J., 369(Pt 2):311-8 (2003).
Luginbuehl, et al. "Localized Delivery of Growth Factors for Bone Repair", Eur. J. of Pharm. and Biopharm. 58(2):197-208(2004).
Lyon, et al., "The Interaction of the Transforming Growth Factor- s with Heparin/ Heparan Sulfate is Isoform-specific," The Journal of Biological Chemistry, 272 (29):18000-18006 (1997).
Maeno, et al., "The effect of calcium ion concentration on osteoblast viability, proliferation and differentiation in monolayer and 3D culture," Biomaterials, 26: 4847-55 (2005).
Martin and Timpl, "Laminin and other basement membrane components," Annu. Rev. Cell.Dev. Biol., 3:57-85 (1987).
Massia, et al., "An RGD spacing of 440 nm is sufficient for integrin alpha V beta 3-mediated fibroblast spreading and 140 nm for focal contact and stress fiber formation," J. Cell. Biol. 114(5):1089-100 (1991).
Maysinger, et al., "Microencapsulated nerve growth factor: effects on the forebrain neurons following devascularizing cortical lesions," Neuroscience Letters, 140:71-74 (1992).
Mccaffrey, et al., "Transforming growth factor-beta 1 is a heparin-binding protein: identification of putative heparin-binding regions and isolation of heparins with varying affinity for TGF-beta 1," J. Cell Physiol. 152(2):430-40 (1992).
Monsonego, et al., "Factor XIIIa as a nerve-associated transglutaminase", FASEB J., 12(12):1163-71 (1998).
Montgomery, et al., "Human neural cell adhesion molecule L1 and Rat homologue NILE are ligands for integrin 3," J Cell Biol 132:475-485 (1996).
Nehls & Herrmann, "The configuration of fibrin clots determine capillary morphogenesis and endothelial cell migration," Microvascular Research 51:347-364 (1996).
Nesti, et al., "TGF-beta1 calcium signaling increases alpha5 integrin expression in osteoblasts", J Orthop Res., 20(5):1042-9 (2002).
Netzel-Arnett, et al., "Sequence specificities of human fibroblast and neutrophil collagenases," J. Biol. Chem. 266(11):6747-55 (1991).
Nolo, et al., "Developmentally regulated neurite outgrowth response from dorsal root ganglion neurons to heparin-binding growth-associated molecule (HB-GAM) and the expression of HB-GAM in the targets of the developing dorsal root ganglion neurites," Eur. J. Neurosci. 8(8):1658-65 (1996).
Nuss, et al., "An animal model in sheep for biocompatibility testing of biomaterials in cancellous bones", BMC Musculoskeletal Disorders, 7:67 (2006).
Oxland, et al., "Effects of endplate removal on the structural properties of the lower lumbar vertebral bodies", Spine 28(8):771-777 (2003).
Peciorek, et al., Annual fall meeting of the BMES, see poster abstract P2.199, Sep. 26-29, 2007.
Pepper, et al., "Angiogenesis: a paradigm for balanced extracellular proteolysis cell migration and morphogenesis," Enzyme Protein 49:138-162 (1996).
Poole and Reeve, "Parathyroid hormone—a bone anabolic and catabolic agent," Current Opinion in Pharmacology, 5: 612-7 (2005).
Potts, "Parathyroid hormone: past and present", J Endocrinol., 187(3):311-25 (2005).
Powell, et al., "Controlled Release of nerve growth factor from a polymeric implant," Brain Research 515:309-311 (1990).
Presta, et al., "Structure-function relationship of basic fibroblast growth factor: site-directed mutagenesis of a putative heparin-binding and receptor-binding region," Biochem. Biophys. Res. Commun. 185(3):1098-107 (1992).
Reddi, "Role of Morphogenetic Proteins in Skeletal Tissue Engineering and Regeneration," Nature Biotechnol., 16:247-252 (1998).
Rixon, et al., "Do the non-catalytic polysaccharide-binding domains and linker regions enhance the biobleaching properties of modular xylanases?" Appl. Microbiol. Biotechnol. 46(5-6): 514-520 (1996).
Rixon, et al., "Parathyroid hormone fragments may stimulate bone growth in ovariectomized rats by activating adenylyl cyclase", J Bone Miner. Res., 9 (8):1179-89 (1994).
Rogers, et al., "Neuron-specific interactions with two neurite-promoting fragments of fibronectin," J. Neurosci. 5(2):369-78 (1985).
Rosengart, et al., "Angiogenesis Gene Therapy. Phase I assessment of direct intramyocardial administration of an adenovirus expressing phVEGF165 cDNA to individuals with clinically significant severe coronary artery disease," Circulation, 100:468-474 (1999).
Rout, et al., "Transforming growth factor-beta1 modulates expression of adhesion and cytoskeletal proteins in human peritoneal fibroblasts", Fertil Steril., 78(1):154-61 (2002).
Ruoslahti & Engvall, "Perspectives series: Cell adhesion in vascular biology," J Clin Invest, 99:1149-1152 (1997).
Sakata & Aoki, et al., "Cross-linking of 2-plasmin inhibitor to fibrin by fibrin-stabilizing factor," J Clin Invest 65:290-297 (1980).
Sakiyama, et al., "Incorporation of heparin-binding peptides into fibrin gels enhances neurite extension: an example of designer matrices in tissue engineering," FASEB J 13(15): 2214-24 (1999).
Sakiyama-Elbert, et al., "Development of fibrin derivatives for controlled release of heparin binding growth factors," J. Controlled Release, 65(3) 389-402 (2000).
Sakiyama-Elbert, et al., "Development of growth factor fusion proteins for cell-triggered drug delivery" FASEB J. 15:1300-1302 (2001).
Sakiyama-Elbert and Hubbell, "Controlled release of nerve growth factor from a heparin-containing fibrin-based cell ingrowth matrix" Journal of Controlled Release 69:149-158 (2000).
Saraph, et al., "Treatment of unicameral calcaneal bone cysts in children review of literature and results using a cannulated screw for continuous decompression of the cyst", J Pediatr. Orthop., 24(5):568-73 (2004).
Schense, et al., "Cross-linking exogenous bifunctional peptides into fibrin gels with factor XIIIa," Bioconjug. Chem., 10(1): 75-81 (1999).
Schense, et al., "Enzymatic incorporation of bioactive peptides into fibrin matrices enhances neurite extension" Nature Biotechnology 18:415-419 (2000).
Schilling, et al., "Osteoclasts and biomaterials," European Journal of Trauma, 2: 107-13 (2006).
Schroeder-Tefft et al., "Collagen and heparin matrices for growth factor delivery," Journal of Controlled Release, 49:291-298 (1997).
Schumacher, et al., "Induction of neoangiogenesis in ischemic myocardium by human growth factors," Circulation, 97:645-650 (1998).
Seibel, et al., Transfection of mitochnondria: strategy towards a gene therapy of mitochondrial DNA diseases, Nucleic Acids Res., 23(1): 10-7 (1995).
Sellke, et al., "Basic FGF enhances endothelium-dependent relaxation of the collateral-perfused coronary microcirculation," Am. J. Physiol. 267(4 Pt 2):H1303-11 (1994).
Shin, et al., "Expression of EphrinB2 identifies a stable genetic difference between arterial and venous vascular smooth muscle as well as endothelial cells, and of adult neovascularization," Developmental Biology 230:139-150 (2001).
Shireman, et al., "Modulation of vascular cell growth by local cytokine delivery from fibrin glue suspensions," J Vasc Surg, 19:852-62 (1999).

(56) References Cited

OTHER PUBLICATIONS

Sierra, "Fibrin sealant adhesive systems: a review of their chemistry, material properties and clinical applications", Journal of Biomaterials Applications, 7:309-352 (1993).
Smith, "Fibrinogen-fibrin conversion. The mechanism of fibrin-polymer formation in solution", Biochemistry J., 185:1-11 (1980).
Smith et al., "Rapid identification of highly active and selective substrates for stromelysin and matrilysin using bacteriophage peptide display libraries", J. Biol. Chem., 270:6440-6449 (1995).
Spillman, et al., "Defining the interleukin-8-binding domain of heparan sulfate," J. Biol. Chem., 273(25):15487-93 (1998).
Steffen, et al., "Characterization of cell-associated and soluble forms of connective tissue growth factor (CTGF) produced by fibroblast cells in vitro," Growth Factors 15 (3):199-213 (1998).
Stein, et al., "Eph receptors discriminate specific ligand oligomers to determine alternative signaling complexes, attachment, and assembly responses," Genes & Development, 12:667-678 (1998).
Studier, et al., "Use of T7 RNA polymerase to direct expression of cloned genes," Methods Enzymol. 185:60-89 (1990).
Takeshita, et al., "Therapeutic Angiogenesis. A single intraarterial bolus of vascular endothelial growth factor augments revascularization in a rabbit ischemic hind limb model," J Clin Invest 93:662-670 (1994).
Tashiro, et al., "A synthetic peptide containing the IKVAV sequence from the A chain of laminin mediates cell attachment, migration, and neurite outgrowth," J. Biol. Chem., 264 (27):16174-82 (1989).
Tessler, et al., "Heparin modulates the interaction of VEGF165 with soluble and cell associated flk-1 receptors," J. Biol. Chem. 269(17):12456-61 (1994).
Thompson, et al., "Site-directed neovessel formation in vivo," Science, 241:1349-1352 (1988).
Tyler-Cross, et al., "Heparin binding domain peptides of antithrombin III: analysis by isothermal titration calorimetry and circular dichroism spectroscopy," Protein Sci. 3(4):620-7 (1994).
Usui, et al., "Propolypeptide of von Willebrand factor serves as a substrate for factor XIIIa and is cross-linked to laminin", J Biol Chem., 268(17):12311-6 (1993).
Wang, et al., "Molecular distinction and angiogenesis interaction between embryonic arteries and veins revealed by ephrin-B2 and its receptor Eph-B4," Cell 93:741-753 (1998).
Weatherford, et al., "Vascular endothelial growth factor and heparin in a biologic glue promotes human aortic endothelial cell proliferation with aortic smooth muscle cell inhibition," Surgery, 433-439 (1996).
Williams, et al., "Exogenous matrix precursors promote functional nerve regeneration across a 15-mm gap within a silicone chamber in the rat", Journal of Comparative Neurobiology, 264:284-290 (1987).
Yamada, et al., "Characterization of fibronectin interactions with glycosaminoglycans and identification of active proteolytic fragments", J Biol Chem., 255(13):6055-63 (1980).
Yamada, "Adhesive recognition sequences," J. Biol. Chem. 266(20):12809-12 (1991).
Yanish-Perron, et al., "Improved M13 phage cloning vectors and host strains: nucleotide sequences of the M13mp18 and pUC19 vectors," Gene, 33(1):103-19 (1985).
Zisch, et al., "Covalently conjugated VEGF-fibrin matrices for endothelialization" Journal of Controlled Release 72:101-113 (2001).
Zucker and Katz, "Platelet factor 4: production, structure, and physiologic and immunologic action," Proc. Soc. Exp. Biol. Med., 198(2):693-702 (1991).

* cited by examiner

SEQUENCE LISTING

```
<160> NUMBER OF SEQ ID NOS: 15

<210> SEQ ID NO 1
<211> LENGTH: 5
<212> TYPE: PRT
<213> ORGANISM: Homo sapiens

<400> SEQUENCE: 1

Gly Ala Lys Asp Val
1               5

<210> SEQ ID NO 2
<211> LENGTH: 4
<212> TYPE: PRT
<213> ORGANISM: Homo sapiens

<400> SEQUENCE: 2
```

```
Lys Lys Lys Lys
1

<210> SEQ ID NO 3
<211> LENGTH: 16
<212> TYPE: PRT
<213> ORGANISM: Homo sapiens

<400> SEQUENCE: 3

Tyr Arg Gly Asp Thr Ile Gly Glu Gly Gln Gln His His Leu Gly Gly
1               5                   10                  15

<210> SEQ ID NO 4
<211> LENGTH: 8
<212> TYPE: PRT
<213> ORGANISM: Homo sapiens

<400> SEQUENCE: 4

Asn Gln Glu Gln Val Ser Pro Leu
1               5

<210> SEQ ID NO 5
<211> LENGTH: 6
<212> TYPE: PRT
<213> ORGANISM: Homo sapiens

<400> SEQUENCE: 5

Leu Ile Lys Met Lys Pro
1               5

<210> SEQ ID NO 6
<211> LENGTH: 6
<212> TYPE: PRT
<213> ORGANISM: Homo sapiens

<400> SEQUENCE: 6

Asn Phe Lys Ser Gln Leu
1               5

<210> SEQ ID NO 7
<211> LENGTH: 8
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION

<400> SEQUENCE: 7

Gly Pro Leu Ala Leu Thr Ala Leu
1               5

<210> SEQ ID NO 8
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: AMIDATION

<400> SEQUENCE: 8

Pro Phe Glu Leu Arg Ala
```

```
<210> SEQ ID NO 9
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: AMIDATION

<400> SEQUENCE: 9

Glx Ala Ala Phe Ala
1               5

<210> SEQ ID NO 10
<211> LENGTH: 8
<212> TYPE: PRT
<213> ORGANISM: Homo sapiens

<400> SEQUENCE: 10

Gly Pro Leu Gly Ile Ala Gly Pro
1               5

<210> SEQ ID NO 11
<211> LENGTH: 8
<212> TYPE: PRT
<213> ORGANISM: Homo sapiens

<400> SEQUENCE: 11

Pro His Tyr Gly Arg Ser Gly Gly
1               5

<210> SEQ ID NO 12
<211> LENGTH: 9
<212> TYPE: PRT
<213> ORGANISM: Homo sapiens

<400> SEQUENCE: 12

Pro Gly Ser Gly Arg Ser Ala Ser Gly
1               5

<210> SEQ ID NO 13
<211> LENGTH: 4
<212> TYPE: PRT
<213> ORGANISM: Homo sapiens

<400> SEQUENCE: 13

Tyr Lys Asn Arg
1

<210> SEQ ID NO 14
<211> LENGTH: 46
<212> TYPE: PRT
<213> ORGANISM: Artificial Sequence
<220> FEATURE:
<223> OTHER INFORMATION: Synthetic fusion protein

<400> SEQUENCE: 14

Asn Gln Glu Gln Val Ser Pro Leu Tyr Lys Asn Arg Ser Val Ser Glu
1               5                   10                  15

Ile Gln Leu Met His Asn Leu Gly Lys His Leu Asn Ser Met Glu Arg
            20                  25                  30

Val Glu Trp Leu Arg Lys Lys Leu Gln Asp Val His Asn Phe
        35                  40                  45
```

```
<210> SEQ ID NO 15
<211> LENGTH: 42
<212> TYPE: PRT
<213> ORGANISM: Artificial Sequence
<220> FEATURE:
<223> OTHER INFORMATION: Synthetic fusion protein

<400> SEQUENCE: 15

Asn Gln Glu Gln Val Ser Pro Leu Ser Val Ser Glu Ile Gln Leu Met
1               5                   10                  15

His Asn Leu Gly Lys His Leu Asn Ser Met Glu Arg Val Glu Trp Leu
            20                  25                  30

Arg Lys Lys Leu Gln Asp Val His Asn Phe
            35                  40
```

PHARMACEUTICAL FORMULATION FOR USE IN SPINAL FUSION

CROSS REFERENCE TO RELATED APPLICATIONS

The present application is a continuation of PCT patent application PCT/EP2011/054008, filed Mar. 16, 2011.

REFERENCE TO SEQUENCE LISTING

The Sequence Listing submitted Sep. 7, 2011 as a text file named "KUROS_142_ST25.txt," created on Aug. 22, 2011, and having a size of 3,284 bytes is hereby incorporated by reference.

FIELD OF THE INVENTION

The present application relates to PTH-containing formulations and uses thereof in spinal fusion.

BACKGROUND OF THE INVENTION

Spinal fusion, also known as spondylodesis or spondylosyndesis, is a surgical treatment method used for the treatment of various morbidities such as degenerative disc disease, spondylolisthesis (slippage of a vertebra), spinal stenosis, scoliosis, fracture, infection or tumor. The aim of the spinal fusion procedure is to reduce instability and thus pain. Patients requiring spinal fusion have either neurological deficits or severe pain which has not responded to conservative treatment. Spinal fusion is achieved by instrumentation to stop movement between the vertebrae and involves removal of the intervertebral disc, laminectomy, roughening of the bone surfaces that are required to be fused and application of a material that stimulates bone growth between adjacent vertebrae. It is estimated that each year in the US alone, approximately 500,000 spinal fusion procedures are performed.

The spine has three main segments: the cervical spine, the thoracic spine, and the lumbar spine. The cervical spine is the upper part of the spine, i.e., the neck, and it is made up of seven vertebrae. The thoracic spine is the center part of the spine, and it is made up of 12 vertebrae. The lumbar spine is the lower portion of the spine. It is usually made up of five vertebrae; however, some people have six lumbar vertebrae. Spinal fusion is done most commonly in the lumbar region of the spine, but it is also used to treat problems in the cervical and, more rarely, thoracic spine.

There are two types of spinal fusion, which may be used either alone or in conjunction with each other: (i) posterolateral fusion, which places the material that stimulates bone growth (i.e. the bone graft or bone graft substitutes) on the spinal gutter in the back of the spine. These vertebrae are then fixed in place with screws and or wire through the pedicles of each vertebra attaching to a metal rod on each side of the vertebrae and the bone bridge is formed between the transverse processes of the spine; (ii) Interbody fusion, which places the bone graft or bone graft substitute between the vertebra in the area usually occupied by the intervertebral disc. In preparation for the spinal fusion, the disc is removed entirely. A device, the spinal fusion cage, may be placed between the vertebra to maintain spine alignment and disc height. The interbody cage may be made from synthetic polymers, titanium or other metals or bone. The fusion, i.e. bone bridge, occurs between the endplates of the vertebrae. Fusion rates are usually higher with interbody fusion than with posterolateral fusion.

In most cases, the fusion is augmented by a process called fixation, i.e., the placement of metallic screws (pedicle screws often made from titanium), rods or plates, to stabilize the vertebra to facilitate bone fusion. The main challenge in terms of a clinically successful outcome of a spinal fusion procedure is the need to form bone tissue instead of the original type of tissue in the space between the vertebrae. The original type of tissue in case of interbody fusion is a disc and in the case of a posterolateral fusion, it is muscle tissue. As the bone has to grow and replace a different tissue type, there is a need to create an appropriate environment to trigger and promote bone formation in this area.

A bone graft is needed to create the appropriate environment in order for a solid bone bridge to form between the vertebrae. Currently, bone grafts and a variety of bone graft substitutes are used in spinal fusion, with mixed clinical outcomes. A variety of materials may serve as bone grafts or bone graft substitutes, including autografts (harvested from the iliac crest of the patient's body), allografts, demineralised bone matrix, and various synthetic materials. The synthetic materials include calcium phosphates or hydroxyapatites, stem cell containing products which combine stem cells with one of the other classes of bone graft substitutes, and as the latest generation of bone graft substitutes, growth factor containing matrices such as INFUSE® (rhBMP-2-containing bone graft) from Medtronic Sofamor Daniek, Inc. Autograft is the gold standard in this indication because of efficacy and safety. However, due to limited supply of a patient's own bone, the risk of donor site pain and morbidity (blood loss, infection) in combination with long hospital stays and operation time, there has been a continued search for bone graft substitutes to replace autologous bone. Growth factor containing matrices, for example, INFUSE®, have demonstrated equivalent fusion rates to autograft and have therefore had significant impact on the market. However, there are disadvantages associated with this product. In addition to the expensive production process of the BMP (bone morphogenetic protein), the protein is delivered from a collagen matrix in high concentration. Collagen matrices from bovine origin carry the risks associated with xenogenic materials, i.e. disease transmission, and show poor handling properties in the surgical procedure, e.g., they are not moldable to closely fit to the shape of the injury or fusion site. Further, the high concentration of BMPs delivered to the body can lead to calcification of organs or to bone formation in other parts of the body, so called ectopic bone formation. In particular, several complications related to the use of BMP-2 in spinal fusion have been reported (e.g., neurological complications induced by exuberant bone formation, as well as respiratory complications due to inflammatory response/swelling around the application site) (Epstein, Surgical Neurology International, 2:10 (2011)). In July 2008 the FDA issued a safety notice relating to the use of INFUSE® in the cervical spine.

It is an object of the present invention to provide a bone graft substitute which effectively fuses vertebrae in spinal fusion procedures and is safer to use than the currently available bone graft substitutes.

It is a further object of the present invention to provide a bone graft substitute that is easy to prepare and apply (i.e., allows for easy handling) during an operation procedure.

It is still a further object of the present invention to provide a bone graft substitute that allows the application of the product during operation without additional damage to the surrounding tissue.

It is still an object of the present invention to provide an improved method for spinal fusion.

It is also an object of this invention to provide a kit for use in treating spinal fusion.

It is also an object of this invention to provide an improved fusion cage for spinal fusion, in particular for interbody spinal fusion.

SUMMARY OF THE INVENTION

A pharmaceutical formulation and a pharmaceutical product for use in a spinal fusion method, an interbody spinal fusion cage comprising the pharmaceutical product, a kit for use in a spinal fusion method, and a method for forming a pharmaceutical product for use in a spinal fusion method are provided herein.

The pharmaceutical formulation for use in a spinal fusion method comprises a composition for forming a pharmaceutical product, for use in a spinal fusion method. The composition for forming the pharmaceutical product comprising at least a first matrix material precursor component and a second matrix material precursor component, where the precursor components are capable of forming a matrix by crosslinking under appropriate conditions. The composition also contains a bioactive factor. The pharmaceutical product for use in a spinal fusion method, comprises a matrix and a bioactive factor releasably incorporated therein.

The bioactive factor is a biologically active agent that can stimulate bone formation between two vertebrae, for effecting and/or supporting spinal fusion. In one embodiment, the bioactive factor is a parathyroid hormone (PTH). PTH containing peptides are also included in the definition of PTH. The PTH is preferably $PTH_{1-34}$. In another preferred embodiment the PTH is a fusion peptide containing PTH. In this embodiment, the PTH fusion peptide preferably contains at least two domains wherein the first domain comprises PTH and the second domain comprises a crosslinkable substrate domain. The crosslinkable substrate domain is a transglutaminase substrate domain, more preferably, a Factor XIIIa substrate domain. The PTH fusion peptide preferably further comprises an enzymatic or hydrolytic degradation site between the first and the second domains. In a further preferred embodiment the PTH is the only added peptide or proteinaceous bioactive factor in the composition and/or product with bone forming properties.

The matrix can be comprised of a variety of materials. In one embodiment the matrix is made of ceramics, i.e. inorganic materials, like hydroxyapatites, tricalciumphosphate or combinations thereof, calcium sulphate or bioglass. In another embodiment the matrix is made of organic materials such as glycoproteins, for example, collagen, polysaccharides or glycosaminoglycans, such as hyaluronic acid or combinations of different organic materials. In a preferred embodiment the matrix is comprised of fibrin or polyoxyalkylenes. The matrix can be formed by matrix precursor components which assemble to form the matrix by van-der Waals forces, by ionic or covalent bonds, or adherence, by sintering or combinations thereof.

In a preferred embodiment the matrix is formed in situ at mixing and/or the site of application in the body. The matrix can also be formed outside the body, cut to the appropriate shape and/or be further optimized, e.g. by water uptake, i.e. swelling, such as collagen sponges.

The matrix is preferably formed from a composition comprising at least a first matrix material precursor component and a second matrix material precursor component, where the precursor components are capable of forming a matrix by crosslinking under appropriate conditions. In one embodiment, the first and second precursor components are naturally occurring molecules such as proteins. In a preferred embodiment, the first component is fibrinogen, and the second component is thrombin. In another embodiment, the first and second components are made of synthetic materials, for example, functionalized polyoxyalkylenes. The compositions of the preferred embodiment may further contain a biodegradable ceramic compound, preferably in the form of granules. Preferred biodegradable ceramic compounds are porous calcium containing materials. The ceramic compounds may provide structural support to the resulting matrix. In a preferred embodiment the pharmaceutical product is made from the pharmaceutical formulations described herein and is used for the stimulation of spinal fusion, preferably, interbody spinal fusion.

The matrices preferably allow for cell ingrowth and proliferation and thus have interstitial spacing for cells to migrate and proliferate through the matrix.

In a preferred embodiment, the pharmaceutical product is used in combination with an interbody cage, which may be formed of a variety of materials, including but not limited to Poly-Ether-Ether-Ketone (PEEK), carbon fiber reinforced polymer (CFRP), titanium etc. Preferably, the interbody cage is made of PEEK or CFRP.

The method of making the pharmaceutical product preferably includes the steps of (i) providing a first matrix material precursor component, (ii) providing a second matrix material precursor component, (iii) providing a bioactive factor, and (iv) mixing the first and the second matrix material precursor components and the bioactive factor, preferably under physiological conditions, to form a matrix material by crosslinking of the first and second matrix material precursor components, and releasably incorporating the bioactive factor in the matrix material. In some embodiments, the method includes adding a granular material prior to, simultaneous with or subsequent to mixing the precursor components and the bioactive factor. In another preferred embodiment the method of making the pharmaceutical product comprises the steps of: (i) cutting an already formed matrix into the desired shape, (ii) soaking the matrix in a bioactive factor containing buffer solution in order for the bioactive factor to become adsorbed or attached to the matrix by van-der-Waals forces or ionic interaction, and (iii) optionally introducing the matrix into the spinal fusion cage. The bioactive factor is a biologically active agent that can stimulate bone formation between two vertebrae, for effecting and/or supporting spinal fusion. In one embodiment, the bioactive factor is a parathyroid hormone (PTH).

The kit provided herein for use in a spinal fusion treatment method contains a matrix or matrix material precursor components and a PTH. In a preferred embodiment the kit contains at least a first and a second matrix material precursor component in a first and second container, respectively. In the later preferred embodiment the kit further comprises a PTH in one of the first or the second matrix material precursor components. In some embodiments, the kit additionally contains a granular material in a third container. In one embodiment the kit additionally comprises a spinal fusion cage.

DETAILED DESCRIPTION OF THE INVENTION

I. Definitions

Figure 1:
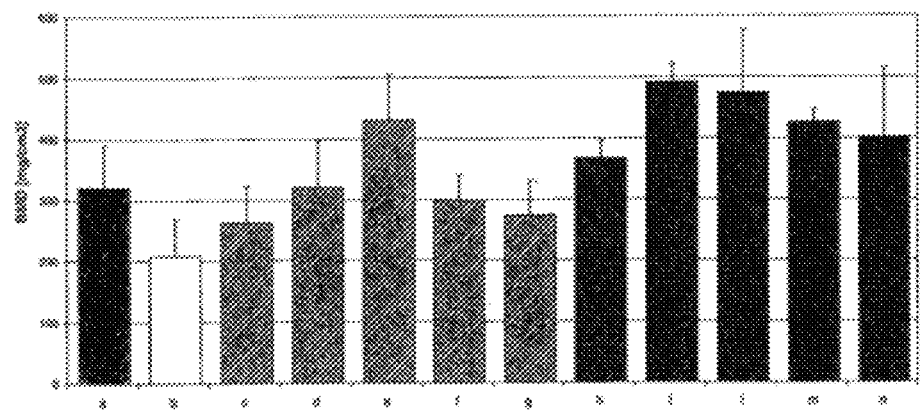
FIG. 1 is a bar graph showing bone mineral densities (BMD) ($mg/cm^3$) obtained with different PTH formulations in a sheep anterior cervical interbody fusion model. Autograft (a); empty (b); 0 mg $TGplPTH_{1-34}$/mL fibrin matrix (c); 0.2 mg $TGplPTH_{1-34}$/mL fibrin matrix (d); 0.4 mg $TGplPTH_{1-34}$/mL fibrin matrix (e); 0.7 mg $TGplPTH_{1-34}$/mL fibrin matrix (f); 1 mg $TGplPTH_{1-34}$/mL fibrin matrix (g); 0 mg $TGplPTH_{1-34}$/mL fibrin matrix+granular material (h); 0.2 mg $TGplPTH_{1-34}$/mL fibrin matrix+granular material (i); 0.4 mg $TGplPTH_{1-34}$/mL fibrin matrix+granular material (j); 0.7 mg $TGplPTH_{1-34}$/mL fibrin matrix+granular material (m); and 1 mg $TGplPTH_{1-34}$/mL fibrin matrix+granular material (n).

"Biological activity" as generally used herein refers to functional events mediated by a peptide or protein of interest. In some embodiments, this includes events assayed by measuring the interactions of a peptide or protein with another polypeptide or protein. It also includes assaying the effect which the peptide or protein of interest has on cell growth, differentiation, death, migration, adhesion, interactions with other proteins or peptides, enzymatic activity, protein phosphorylation or dephosphorylation, transcription, or translation.

"Branched PEG" as used herein refers to polyethylene glycol with more than two ends.

"Calcium mineral" as generally used herein refers to substances which contain calcium ions. An example of a calcium mineral is hydroxyapatite ($Ca_5[(OH)(PO_4)_3]$) which is the main component of teeth and bones.

"Cross-linking" as generally used herein means the formation of covalent links between two or more molecules.

"Electrophilic group", as used herein, refers to molecule which is capable of accepting an electron pair from a nucleophile in a polar-bond forming reaction. The terms "electrophile" and "electrophilic group" are used synonymously.

"Fibrin matrix" as generally used herein means the product of a process in which the precursor components fibrinogen and thrombin partially or fully crosslink in the presence of a calcium source and Factor XIIIa. The crosslinked fibrin precursor components, even when partially crosslinked, form a three dimensional network.

"Fusion" as used herein means continuous bone formation from one vertebrae to another as demonstrated in human patients by X-ray and computed tomography (CT) scanning at various timepoints and in animals by micro computed tomography (μCT) and/or X-ray at various timepoints.

"Interbody cage" as used herein refers to a device specifically designed to be implanted in the interbody space during spinal fusion to help restore correct spine alignment and to help maintain disc space height.

"Linear PEG" as used herein means a polyethylene glycol with two ends.

"Matrix" as generally used herein refers to a material intended to interface with biological systems to treat, augment, or replace any tissue or function of the tissue depending on the material either permanently or temporarily. The terms "matrix", "gel", "three-dimensional network", "biomaterial network" interchangeably, and encompass partially or fully crosslinked matrices. The matrix may be in the form of a liquid, semi-solid, such as a paste, or a solid.

"Parathyroid Hormone" (PTH) as used herein includes the human sequence of $PTH_{1-84}$ and all truncated, modified and allelic versions of PTH which exhibit bone formation properties, in particular when incorporated (preferably covalently bound) in a matrix. In the context of the present invention and if not otherwise specifically indicated "PTH" is used as a summary term for all versions of PTH, and includes PTH containing peptides, such as PTH fusion peptides.

"Pharmaceutical formulation" as used herein means a pharmaceutical formulation comprising a composition for forming a matrix, and a bioactive factor which is a PTH. The pharmaceutical formulation comprises the composition in an unassembled form, the matrix precursor components are not assembled to form a matrix.

"Pharmaceutical product" as used herein means a matrix and a bioactive factor releasably incorporated therein.

"PTH fusion peptide" as generally used herein refers to a peptide which contains at least a first and a second domain. One domain contains a PTH, preferably $PTH_{1-34}$ and the other domain contains a substrate domain crosslinkable to a matrix during or after its formation.

"PTH Supplemented Matrix" as generally used herein means a matrix in which PTH is releasably incorporated therein. PTH is incorporated through covalent and/or non-covalent interactions.

"Spinal fusion" as used herein refers to a surgical procedure aimed at achieving bone formation and thereby fusion between two or more adjacent vertebrae.

"Strong nucleophile", as used herein, refers to a molecule which is capable of donating an electron pair to an electrophile in a polar-bond forming reaction. Preferably the strong nucleophile is more nucleophilic than $H_2O$ at physiologic pH. Examples of strong nucleophiles are thiols and amines.

II. Pharmaceutical Products for Use in Spinal Fusion

Although locally delivered PTH in fibrin has been reported to be suitable for the repair of bone fractures, for treatment of solitary bone cysts (SBC) and to increase bone mass in osteoporotic patients (see WO 2006/072622 and WO 2006/072623), it was not shown that PTH in matrices, locally delivered to the site of need would show fusion of two adjacent vertebrae in a spinal fusion procedure. The previous studies did not include spinal fusion and the results in those studies could not be extrapolated to spinal fusion for several reasons.

First, each healing environment has unique features. Therefore a bone graft or bone graft substitute must be tested in each specific healing environment to predict efficacy in that environment. (Boden, *Spine*, 27(16S):S26-S31 (2002)). This principle is also applied by the U.S. Food and Drug Administration (FDA). Different healing environments like, for example, metaphyseal defects, long bone fractures, and interbody spine fusion have increasing levels of difficulty in forming new bone. Thus validation of any bone graft or bone graft substitute in one clinical anatomic site is not predictive of its performance in another location (Boden, 2002).

Second, bone formation to repair bone fractures involves different biological processes than bone formation in spinal fusion. For example, fracture healing is a proliferative physiological process in which the body facilitates the repair of a bone fracture. The body responds to the traumatic event with production of several growth factors in a timely manner. These growth factors are able to attract stem cells and stimulate their proliferation and differentiation into osteoblasts, and ultimately induce bone healing. In contrast, spinal fusion is a surgical procedure intended to achieve bone formation and fusion within two segments of the spine. Therefore there is a need to stimulate de novo bone formation in spinal fusion.

In order for a material to be able to induce de novo bone formation, it must contain one or more growth factors that are able to induce differentiation of progenitor cells into osteoblasts (Boden, 2002). BMPs have the ability to induce de novo bone formation when applied intramuscularly in rat (Hsu, *Journal of orthopaedic research*, 1660-1669 (2006)), therefore their efficacy in spinal fusion was expected. The formation of ectopic bone using rat ectopic bone assay is a standard method for determining whether a material is able to induce de novo bone formation (Boden, 2002). As described by the examples herein, PTH releasably incorporated in a matrix does not induce ectopic bone formation, and therefore would not be expected to be able to stimulate interbody spinal fusion. However, as shown herein by the examples, spinal fusion was achieved by presenting PTH in a suitable matrix allowing controlled release of the PTH incorporated therein, and placing the matrix having PTH releasably incorporated therein between the adjacent vertebrae to be fused preferably by incorporating the PTH supplemented matrix in a spinal fusion cage.

The pharmaceutical formulations and pharmaceutical products disclosed herein are preferably used in an interbody spinal fusion procedure, to obtain fusion of adjacent vertebra. Pharmaceutical products described herein comprises a matrix and a bioactive factor releasably incorporated therein. The bioactive factor can be PTH. The PTH is preferably the only added peptide or proteinaceous bioactive factor in the product with bone forming properties. In a preferred embodiment the pharmaceutical product is made from the pharmaceutical formulation and used in a spinal fusion method. In order to be a pharmaceutical product the matrix is in a partially or completely assembled stage, i.e. in case of covalent bonds the matrix precursor components are in a partly or fully crosslinked stage.

Preferably, the pharmaceutical formulations or product is applied to an anatomical location or space where bone tissue has to be formed, to fuse and stabilize the vertebrae. A preferred location is the disc space, and the pharmaceutical product or formulation is preferably applied in conjunction with an interbody cage.

A. Matrices

One function of the matrix is to deliver PTH. In preferred embodiment the matrix has interstitial spacing and allows cells to proliferate and migrate and thus can also gives structural support. The matrix can be made from already naturally existing materials, such as by extraction, purification, hydration and/or cutting into the desired shape and if required can be further optimized by soaking in buffer solution for to increase the water content of the matrix by swelling or applying coatings to modify surface properties. The matrix can also be formed from precursor components by chemical reactions or physical interactions so that the precursor components assemble to form a matrix material. The type of precursor component dictates the reaction conditions for forming the matrix. The formation of the matrix can happen before use, during or after preparing and administering to the site of need. When the matrix is formed by matrix precursor components the components assemble to form the matrix by van-der Waals forces, by ionic or covalent bonds, or adherence, by sintering or combinations thereof. Preferably the matrix is formed by covalent cross-linking of at least a first and second matrix material precursor component. Suitable matrix materials and matrices are disclosed in WO 00/44808 A1 and WO 03/052091 A1, the disclosure of which are incorporated herein by reference.

In one embodiment the matrix is formed from proteins, preferably proteins naturally present in the patient into which the matrix is to be implanted. Examples of proteinacious materials that can be used as matrix materials include fibrin, collagen and gelatine. Polysaccharides, glycoproteins, and glycosaminoglycans, like hyaluronic acid and ceramics or combinations thereof may also be used.

In a preferred embodiment the matrix is a fibrin matrix. In another preferred embodiment the matrix is a polyalkylene-oxide based synthetic material, preferably a polyethylene oxide-based material. Exemplary materials include linear or branched polyoxyalkylenes, in particular polyethyleneglycols, which are functionalized with either a strong nucleophile, such as a thiol, or a conjugated structure, such as an acrylate or a vinyl sulfone.

Depending on the type of precursor materials, the matrix may be swollen with water but not dissolved in water, i.e. form a hydrogel which stays in the body to enable bone formation from one vertebrae to another. The matrix can also further contain a biodegradable ceramic compound, preferably in the form of granules, in case the matrix is made of materials different to ceramics. Preferred biodegradable ceramic compounds are porous calcium containing materials. The ceramic compounds may provide structural support to the resulting matrix.

a. Fibrin Matrices

Fibrin is a natural material which has been reported for several biomedical applications. Matrices made from fibrin have been described as material for cell in-growth matrices in U.S. Pat. No. 6,331,422 to Hubbell et al. Fibrin has been used in sealants because of its ability to bind to many tissues and its natural role in wound healing. Some specific applications include use as a sealant for vascular graft attachment and heart valve attachment (Sierra, *Journal of Biomaterials Applications*, 7:309-352 (1993). Additionally, these matrices have been used as drug delivery devices, and for neuronal regeneration (Williams, et al., *Journal of Comparative Neurobiology*, 264:284-290 (1987) and US Publication No. 2004/0082513). Although fibrin matrices provide a solid support for tissue regeneration and cell in-growth, there are few active sequences in the fibrin matrix that directly enhance these processes.

i. Fibrin Structure and Matrix Formation In Vivo

Fibrinogen consists of two tripeptide units with structure. The complete molecule has an ', ' and ' subunit configuration.

The two tripeptide structures are covalently linked by disulfide bonds. Devlin, in Textbook of Biochemistry, 3$^{rd}$ ed. Wiley-Liss, MY 1992, page 968. The process by which fibrinogen is polymerized into fibrin has been characterized. Initially, a protease cleaves the dimeric fibrinogen molecule at two symmetric sites. There are several possible proteases than can cleave fibrinogen. The proteases include thrombin, peptidase, and protease III. Each of these proteases severs the fibrinogen at a different site. Thrombin converts fibrinogen to fibrin monomers by cleaving fibrinopeptides A (16 amino acid residues) and B (14 amino acid residues) from the N-terminal ends of the Aα and Bβ chains, respectively. Smith, *Biochemistry J.*, 185(i):1-11 (1980). Once the fibrinogen is cleaved, a self-polymerization step occurs in which the fibrinogen monomers come together and form a non-covalently crosslinked polymer gel. This self-assembly happens because binding sites become exposed after protease cleavage occurs. Once they are exposed, these binding sites in the centre of the molecule can bind to other sites on the fibrinogen chains, which are present at the ends of the peptide chains. In this manner, a polymer network is formed. Factor XIIIa, a transglutaminase activated from Factor XIII by thrombin proteolysis, may then covalently crosslink the polymer network. Other transglutaminases exist and may also be involved in covalent crosslinking or grafting to the fibrin network.

ii. Degradation of Fibrin Matrices In Vivo

Once a crosslinked fibrin matrix is formed, the subsequent degradation is tightly controlled. One of the key molecules in controlling the degradation of fibrin is α2-plasmin inhibitor. This molecule acts by crosslinking a chain of fibrin through the action of Factor XIIIa. By attaching itself to the matrix, a high concentration of inhibitor can be localized to the matrix. The inhibitor then acts by preventing the binding of plasminogen to fibrin and inactivating plasmin. The α2-plasmin inhibitor contains a glutamine substrate. The exact sequence has been identified as NQEQVSPL (SEQ ID NO: 1), with the first glutamine being the active amino acid for crosslinking.

iii. Fibrin Matrix Precursor Components

The fibrin matrix is preferably formed from two matrix precursor components which can be in the form of solutions, or lyophilized and dissolved prior to mixing or during mixing by the solution of the other matrix precursor component. The first matrix precursor component, typically in a form of a solution, contains fibrinogen, preferably in a concentration range from 10 to 130 mg fibrinogen per millilitre precursor solution, more preferably from 30 to 120 mg fibrinogen per millilitre precursor solution, even more preferably from 50 to 110 mg fibrinogen per millilitre precursor solution, and most preferably from 60 to 90 mg fibrinogen per millilitre precursor solution.

If thrombin has to be added to form the matrix, the second matrix precursor component, also typically in form of a solution, contains thrombin, preferably in a concentration range from 1 to 10 I.U. thrombin per millilitre precursor solution, more preferably from 2.5 to 6.5 I.U. thrombin per millilitre precursor solution, most preferably from 3 to 5 I.U. thrombin per millilitre precursor solution. I.U. stands for one international unit of thrombin and is defined as the activity contained in 0.0853 mg of the First International Standard of Human Thrombin.

Additionally a calcium ion source is in one of the matrix precursor solutions. The calcium ion source is preferably $CaCl_2 \cdot 2H_2O$ in a concentration range from 1 to 10 mg per ml precursor solution, even more preferably from 4 to 7 mg per ml precursor solution, most preferably from 5 to 6 mg per ml precursor solution. Optionally, an enzyme capable of catalyzing the matrix formation, like Factor XIIIa, is added to a precursor solution, preferably to the fibrinogen precursor solution. Preferably, Factor XIIIa is present in a concentration range from 0.5 to 100 I.U. per millilitre precursor solution, more preferably from 1 to 60 I.U. per millilitre precursor solution, and most preferably from 1 to 10 I.U. per millilitre precursor solution.

This composition does not take into account any water used to wet any potential granules before mixing into fibrin matrix since said water stays in the pores of the granules throughout the process of matrix formation and thus does will not have any dilutive effect on the fibrinogen and thrombin concentration in the fibrin matrix.

Fibrinogen and thrombin are preferably stored separately in lyophilised form (either of which can contain the PTH and/or the granular material) and reconstituted prior to use.

(iv) Fibrin Matrix

In one preferred embodiment, the polymerized fibrin matrix contains fibrin in a range between 5 to 65 mg/mL fibrin matrix, preferably between 15 to 60 mg/mL fibrin matrix, more preferably between 25 to 55 mg/mL fibrin matrix, most preferably between 36 to 50 mg/mL fibrin matrix.

(b) Synthetic Matrices

Crosslinking reactions for forming synthetic matrices comprise (i) free-radical polymerization between two or more matrix material precursor components containing unsaturated double bonds, as described in Hern et al., *J. Biomed. Mater. Res.* 39:266-276 (1998), (ii) nucleophilic substitution reactions such as between a precursor component including an amine group and a precursor component including a succinimidyl group as disclosed in U.S. Pat. No. 5,874,500 to Rhee et al., (iii) condensation and addition reactions, and (iv) Michael type addition reactions between a matrix material precursor component comprising strong nucleophile and a matrix material precursor component comprising conjugated unsaturated group or bond (as a strong electrophile).

Michael type addition reactions are described in WO00/44808, the content of which is incorporated herein by reference. Michael type addition reactions allow for in situ crosslinking of at least a first and a second matrix material precursor component under physiological conditions in a self-selective manner, even in the presence of sensitive biological materials. When one of the matrix material precursor components has a functionality of at least two, and at least one of the other matrix material precursor components has a functionality greater than two, the system will self-selectively react to form a cross-linked three dimensional matrix. Michael type addition reactions are preferably between a strong nucleophile (e.g., thiol or amino groups) and a strong electrophile (e.g., conjugated unsaturated groups, such as acrylate or vinyl sulfone groups). Particularly preferred is the reaction between a matrix material precursor component having a thiol or amine group as the nucleophilic group, and a matrix material precursor component having an acrylate or vinyl sulfone groups as electrophilic groups. Preferably, the conjugated unsaturated groups or conjugated unsaturated bonds are acrylates, vinylsulfones, methacrylates, acrylamides, methacrylamides, acrylonitriles, 2- or 4-vinylpyridinium, maleimides, or quinones.

The nucleophilic groups are preferably thiol-groups, amino-groups or hydroxyl-groups. Thiol groups are substantially more reactive than unprotonated amine groups. The most preferred nucleophilic group is the thiol group.

The pH affects the relative reactivity of the nucleophilic groups: the deprotonated thiol is substantially more reactive than the protonated thiol. Therefore, the addition reactions involving a conjugated unsaturation, such as an acrylate or a quinone, with a thiol to convert two matrix material precursor components into a matrix, will often be best carried out most quickly and self-selectively in an alkaline environment, starting at a pH of approximately 8. At pH around 8, most of the thiols are deprotonated (and thus more reactive) and most of the amines of interest are still protonated (and thus less reactive). When a thiol is used as the first precursor molecule, a conjugate structure that is selective in its reactivity for the thiol relative to amines is highly desirable.

In some embodiments, the matrix is a synthetic matrix or a mixed synthetic/natural matrix, and the composition for forming the matrix comprises a matrix material precursor component having strong nucleophilic groups or bonds, and a matrix material precursor component having strong electrophilic groups or bonds.

Synthetic Matrix Material Precursor Components

Suitable first and second matrix material precursor components include proteins, peptides, polyethylene glycol (PEG), polyoxyalkylenes, poly(vinyl alcohol), poly(ethylene-co-vinyl alcohol), poly(acrylic acid), poly(ethylene-co-acrylic acid), poly(ethyloxazoline), poly(vinyl pyrrolidone), poly(ethylene-co-vinyl pyrrolidone), poly(maleic acid), poly(ethylene-co-maleic acid), poly(acrylamide), and poly(ethylene oxide)-co-polypropylene oxide) block copolymers. A particularly preferred matrix material precursor component is based on polyethylene glycol (PEG) such as functionalized PEG.

Polyethylene glycol provides a convenient building block. One can readily purchase or synthesize linear or branched PEGs and then functionalize the PEG end groups to introduce either a strong nucleophile, such as a thiol, or a conjugated structure, such as an acrylate or a vinyl sulfone. When these components are either mixed with each other or with a corresponding component in a slightly basic environment, a matrix will be formed by reaction between the first and the second precursor component, i.e. between the thiol and the acrylate or vinylsulfone. A PEG matrix precursor component can be reacted with a non-PEG matrix precursor component, and the molecular weight or hydrophilicity of either component can be controlled to manipulate the mechanical characteristics, the permeability, and the water content of the resulting matrix.

In the formation of matrices, especially matrices that are designed to degrade in vivo, peptides also provide a convenient building block. It is straightforward to synthesize peptides that contain two or more cysteine residues, and this component can then readily serve as the first matrix precursor component with nucleophilic groups, i.e., thiol groups. For example, a peptide with two free cysteine residues will readily form a matrix when mixed with a PEG tri-vinylsulfone (a PEG having three arms with vinylsulfones at each of its arms) at physiological or slightly higher pH (e.g., 8 to 9). The gelation can also proceed well at even higher pH, but at the potential expense of self-selectivity. When the two liquid precursor components are mixed together, the crosslinking time can be tailored between a few seconds to several minutes to form an elastic gel, consisting of a network of PEG chains, bearing the nodes of the network, with the peptides as connecting links.

The peptides can be selected as protease substrates, so as to make the network capable of being infiltrated and degraded by cells, as is done in a protein-based network, such as in a fibrin matrix. Preferably the sequences in the domains are substrates for enzymes that are involved in cell migration (e.g., substrates for enzymes such as collagenase, plasmin, metalloproteinase (MMP) or elastase), although suitable domains are not limited to these sequences. One particularly useful sequence is a substrate for the enzyme plasmin. The degradation characteristics of the gels can be manipulated by changing the details of the peptide that serves as the cross-linking nodes. One may make a matrix that is degradable by collagenase, but not plasmin, or by plasmin, but not collagenase. Furthermore, it is possible to make the gel degrade faster or slower in response to such an enzyme, simply by changing the amino acid sequence so as to alter the $K_m$ or $k_{cat}$, or both, of the enzymatic reaction. One can thus make a matrix that is biomimetic, in that it is capable of being remodeled by the normal remodeling characteristics of cells. For example, such a study shows substrate sites for the important protease plasmin. The gelation of the PEG with the peptide is self-selective.

Matrices formed from reaction of precursor components having acrylates as functional groups and precursor components having thiols as functional groups, contain hydrolytically degradable ester bonds. Other matrix types might need the addition of hydrolytic or enzymatic degradable linkages. Having protease substrates incorporated into the matrix can be an important when the matrix is formed from matrix precursor components having functional groups like vinylsulfones, which do not lead to linkages that are hydrolytically degradable after reaction with nucleophiles like thiols or amines. Therefore, the incorporation of protease substrates allows the matrix to degrade in the body in all the cases in which the reaction of the matrix material precursor components do not lead to hydrolytically degradable bonds.

The synthetic matrices are operationally simple to form. At least two liquid matrix material precursor components are mixed at neutral or alkaline pH environment; one of the liquid components contains a precursor molecule with nucleophilic groups and the other contains the electrophilic groups. Physiological saline can serve as the solvent. Minimal heat is generated by the reaction. Therefore, the gelation can be carried out in vivo or in vitro, in direct contact with tissue, without untoward toxicity. Thus matrix precursor polymers other than PEG may be used either telechelically modified or modified on their side groups.

(c) Ceramic Matrices

In still another embodiment the matrix can be formed from ceramics, i.e., inorganic materials, like hydroxyapatite (HA), tricalciumphosphate (TCP) or combinations thereof, calcium sulphate or bioglass ($SIO_2$, $Na_2O$, $CaO$ and $P_2O_5$). For example a solution containing PTH may be mixed with ceramic granules, powders or pastes such as HA, TCP or HA/TCP mixtures and allowed to equilibrate. After equilibration supernatant may be collected and the ceramic material may be separated by suitable means, such as centrifugation. Preferably the PTH is $PTH_{1-34}$. The PTH is non covalently adsorbed onto the ceramic matrix—A fusion peptide is not needed to attach the PTH to the ceramic matrix. For example different concentrations of PTH such as 1.0, 0.5, 0.25, 0.1, 0.05 mg $PTH_{1-34}$/ml water of buffer solution were mixed with HA/TCP granules. It was found using Ultraviolet-visible (UV.Vis) spectroscopy (scanned at 280 nm), that approximately 25% of the amount of $PTH_{1-34}$ present in the solution was adsorbed onto the granules with the maximum amount of $PTH_{1-34}$ on the matrix being 1 mg PTH per 1 g of matrix (HA/TCP).

B. PTH

The parathyroid hormone can be $PTH_{1-84}$ (native), $PTH_{1-38}$, $PTH_{1-34}$, $PTH_{1-31}$, or $PTH_{1-25}$, or any modified or allelic versions of PTH exhibiting bone forming properties. Preferred truncated versions of PTH are $PTH_{1-38}$, $PTH_{1-34}$, $PTH_{1-31}$ or $PTH_{1-25}$. Most preferred is $PTH_{1-34}$. Preferably the PTH is human PTH, although PTH from other sources, such as bovine PTH, may be suitable. The concentration of PTH in the matrix is in a range of from 0.01 to 1 mg PTH/mL fibrin matrix, preferably from 0.2 to 0.7 mg PTH/mL fibrin matrix, most preferably 0.4 mg PTH/mL fibrin matrix.

The PTH concentration is in the relation to the matrix without taking into account the potential presence of granules.

PTH Fusion Peptides

It has been demonstrated that bi-domain peptides, which contain a substrate which is crosslinkable to a matrix or matrix precursor components in one domain and a bioactive peptide sequence enable the bidomain peptide to be crosslinked to certain matrices during or after their formation and that this bioactive peptide retains its cellular activity in vitro.

In one preferred embodiment the PTH is a PTH fusion peptide, which comprises at least two domains wherein the first domain comprises PTH and the second domain comprises a crosslinkable substrate domain. The crosslinkable substrate domain is preferably covalently crosslinkable to the matrix during or after its formation. The crosslinkable substrate domain is preferably a domain for an enzyme, preferably, a substrate domain for a transglutaminase ("transglutaminase substrate domain"). The PTH fusion peptide may be produced recombinantly or by chemical synthesis. The $PTH_{1-34}$ fusion peptide is preferably produced by chemical synthesis. The amino acid sequence of the PTH fusion peptide may also contain an enzymatic or hydrolytic cleavage site, such that the PTH can be released with little or no modification to its primary structure.

(i) Transglutaminase Substrate Domains

Transglutaminases catalyse acyl-transfer reactions between the gamma-carboxamide group of protein bound glutaminyl residues and the epsilon-amino group of lysine residues, resulting in the formation of N-epsilon-(gamma-glutamyl)lysine isopeptide side chains bridges. Preferably, the transglutaminase substrate domain is a substrate for a tissue transglutaminase ("tissue transglutaminase substrate domain"). In a more preferred embodiment, the substrate domain is a substrate domain for Factor XIIIa ("Factor XIIIa substrate domain").

Transglutaminase substrate domains and in particular, Factor XIIIa substrate domains are suitable to link the PTH fusion peptide to fibrin matrices or to synthetic matrices during formation of the matrices. In one embodiment, the synthetic matrix precursor components contain pendant primary amino groups which allow the transglutaminase to crosslink the transglutaminase substrate domain of the fusion peptide to the synthetic matrix precursor components. Another way to link the PTH fusion peptide to synthetic matrices is to synthesized the PTH with one or more pendant free thiol groups, preferably, a free cysteine group (which contains a thiol group). The thiol group can react with the synthetic matrix precursor component having electrophilic groups, e.g. acrylate groups and thereby crosslink the fusion peptide to the precursor component which can further react with the other matrix precursor component to form the PTH supplemented matrix. In a preferred embodiment the cysteine group is at the N-terminal end of the PTH.

Transglutaminase substrate domains suitable for use in making the fusion peptides described herein have been described in detail including their amino acid sequences in WO 03/052091 (sequence listing), the content of which is herein incorporated by reference.

The crosslinkable substrate domain may include GAKDV (SEQ ID NO: 1), KKKK (SEQ ID NO: 2), YRGDTIGEGQQHHLGG (SEQ ID NO: 3), or NQEQVSPL (SEQ ID NO: 4).

The most preferred Factor XIIIa substrate domain has an amino acid sequence of NQEQVSPL (SEQ ID NO: 4) and is herein referred to as "TG".

(ii) Degradation Sites of the Fusion Peptide

An enzymatic or hydrolytic degradation site can be present between the first and the second domains of the fusion peptide. The degradation site allows the PTH to be released with little or no modification to the primary peptide sequence. The degradation site is preferably enzymatically degradable, so that the release of the PTH is controlled by cell specific processes, such as localized proteolysis. In addition, it allows PTH to be released at different rates within the same material depending on the location of cells within the matrix. This might also reduce the amount of total $PTH_{1-34}$ needed to achieve the desired effect since its release is controlled by cellular processes (a release on demand), compared to a PTH being injected in a vehicle which released all the PTH at once at the site of need resulting in a major percentage just washed away from the site of need without effecting any biological effect where it is needed. By careful selection of $K_m$ and $k_{cat}$ of the enzymatic degradation site, degradation could be controlled to occur either before or after degradation of the matrix and/or by utilizing similar or dissimilar enzymes to degrade the matrix. These degradable sites allow the engineering of more specific release of PTH from the matrices. The enzymatic degradation site is abbreviated herein as "pl".

(a) Enzymatic Degradation Sites

Proteolytically degradable sites could include substrates for collagenase, plasmin, elastase, stromelysin, or plasminogen activators. Exemplary substrates are listed below. N1-N5 denotes amino acids 1-5 positions toward the amino terminus of the protein from the site were proteolysis occurs. N1'-N4' denote amino acids 1-4 positions toward the carboxy terminus of the protein from the site where proteolysis occurs.

TABLE 1

Sample substrate sequences for protease.

| Protease | N5 | N4 | N3 | N2 | N1 | N1' | N2' | N3' | N4' | Reference |
|---|---|---|---|---|---|---|---|---|---|---|
| Plasmin (SEQ ID NO: 5) | | L | I | K | M | K | P | | | 1 |
| Plasmin (SEQ ID NO: 6) | | N | F | K | S | Q | L | | | 1 |
| Stromelysin (SEQ ID NO: 7) | Ac | G | P | L | A | L | T | A | L | 2 |
| Stromelysin SEQ ID NO: 8 | | Ac | P | F | E | L | R | A | $NH_2$ | 2 |
| Elastase (SEQ ID NO: 9) | | | Z- | A | A | F | A | $NH_2$ | | 3 |
| Collagenase (SEQ ID NO: 10) | | G | P | L | G | I | A | G | P | 4 |

TABLE 1-continued

Sample substrate sequences for protease.

| Protease | N5 | N4 | N3 | N2 | N1 | N1' | N2' | N3' | N4' | Reference |
|---|---|---|---|---|---|---|---|---|---|---|
| t-PA (SEQ ID NO: 11) | P | H | Y | G | R | S | G | G | | 5 |
| u-PA (SEQ ID NO: 12) | P | G | S | G | R | S | A | S | G | 5 |

References:
1. Takagi and Doolittle, *Biochem.*, 14: 5149-5156 (1975).
2. Smith et al., *J. Biol. Chem.*, 270: 6440-6449 (1995).
3. Besson et al., *Analytical Biochemistry*, 237: 216-223 (1996).
4. Netzel-Arnett et al., *J. Biol. Chem.*, 266: 6747-6755 (1991).
5. Coombs et al., *J. Biol. Chem.*, 273: 4323-4328 (1998).

Enzymes that could be used for proteolytic degradation are numerous. Preferably the degradation site is cleavable by an enzyme selected from the group consisting of plasmin and matrix metalloproteinase.

In a preferred embodiment the sequence YKNR (SEQ ID NO: 13) is present between the first domain and the second domain. This sequence is plasmin degradable.

A particular preferred PTH fusion peptide is TGplPTH$_{1-34}$:

(SEQ ID NO: 14)
NQEQVSPLYKNRSVSEIQLMHNLGKHLNSMERVEWLRKKLQDVHNF.

Another preferred PTH fusion peptide is TG-PTH$_{1-34}$ which comprises the amino acids 1-34 of the native PTH as well as a TG (transglutaminase) substrate domain but no degradation site (SEQ ID NO: 15)
NQEQVSPLSVSEIQLMHNLGKHLNSMERVEWLRKKLQDVHNF.

(b) Hydrolytic Degradation Sites

Non-enzymatic degradation substrate can consist of any linkage which undergoes hydrolysis by an acid or base catalyzed mechanism. These substrates can include oligoesters such as oligomers of lactic or glycolic acid. The rate of degradation of these materials can be controlled through the choice of oligomer.

C. Granular Material

When the matrix is made of a soft, non-weight bearing material like a hydrogel, a granular material may be added to the matrix or the matrix precursor components prior to matrix formation. Preferably, the granular material contains a calcium mineral. This granular material is added to support the mechanical properties of the matrix to adapt the matrix to the specific needs of the indication. This is not required if the matrix is made from a weight bearing material, like ceramics in the first place. The granular material can be any biocompatible material providing the necessary mechanical support to the composition, whereby the degree of mechanical support is dependent on the indication. Preferably the granular material is a ceramic compound and thus, in this case, the resulting final matrix is a mixture of two previously described matrix materials, the ceramic and the hydrogel. Biodegradable ceramic compounds have shown favorable properties in the matrix. The ceramic compound preferably comprises a calcium mineral, like hydroxyapatite, calcium phosphate or calcium sulphate. Suitable materials include biodegradable porous mixtures of hydroxyapatite (HA) and tricalciumphosphate (TCP).

Examples of useful granular materials are biodegradable porous mixtures of hydroxyapatite and tricalciumphosphate, like TricOs™ (hydroxyapatite/tricalcium phosphate mixture) from Biomatlante (France), CAMCERAM® (bone replacement substitute) from Cam Implants, Leiden (Netherlands) or Preferred granular materials are e.g. MBCP™-Hydroxyapatite/β-tricalcium phosphate-Microgranules. Most preferred is the mixture of hydroxyapatite (60%) and tricalciumphosphate (40%), marketed under the trade name TricOs™. The sizes of the granules can range from 1 to 2 mm.

It is also possible to use nonporous hydroxyapatite/tricalcium phosphate granules, pure hydroxyapatite granules (porous or nonporous), tricalcium phosphate granules (porous or nonporous), calcium sulfate granules, bone chips (either autograft or allograft) or xenograft bone chips.

III. Kits

A kit is provided, containing at least a first and a second container. The first matrix material precursor component is provided as a first precursor solution in the first container, and the second matrix material precursor component is provided as a second precursor solution in a second container. The kit also contains PTH. The preferred PTH is a PTH fusion peptide. The matrix precursor components and/or PTH can also be stored frozen or lyophilized and reconstituted in a buffer solution prior to mixing. In a preferred embodiment, the first and second containers contain fibrinogen in the first container, thrombin in the second container. In some embodiments a calcium source is present in either the first or the second container. The PTH may be present in either the first or the second container. Optionally, the kit may contain a granular material, preferably containing a calcium mineral, and a crosslinking enzyme, such as Factor XIIIa. The granular material, if present, is provided in a separate container, for example, a syringe.

Fibrinogen and thrombin can be either both or just one of them in lyophilized form. The PTH may be present in either the fibrinogen or the thrombin solution. In a preferred embodiment the fibrinogen solution contains the PTH.

In another embodiment the kit contains PTH, a first linear or branched functionalized synthetic precursor component, such as polyethylene glycol end-functionalized with nucleophilic groups, preferably thiol groups, and a further linear (only if the first precursor component is branched) or branched functionalized synthetic precursor component such as polyethylene glycol end-functionalized with electrophilic groups, such as conjugated unsaturated groups. The kit further contains a base solution which is separated from the other components.

In embodiments for forming a fibrin matrix, the first precursor solution contains between 10 to 130 mg fibrinogen/ml precursor solution, preferably between 30 to 120 mg fibrinogen/ml precursor solution, most preferably between 50 to 110 mg fibrinogen/ml precursor solution. The second precursor solution contains between 1 to 10 I.U. thrombin/ml precursor solution, preferably between 2.5 to 6.5 I.U. thrombin/ml precursor solution. In some embodiments, a calcium ion source, preferably $CaCl_2*2H_2O$ in a concentration of between 1 to 10 mg/ml precursor solution, preferably between 4 to 7 mg/ml precursor solution, most preferably between 5.2 to 6.6 mg/ml precursor solution, is present in either the first or the second precursor solution The PTH or a peptide comprising PTH can be present in either the first or the second precursor solution, preferably in a concentration of between 0.01 to 1 mg PTH/ml total volume first and second precursor solutions, more preferably between 0.2 to 0.7 mg PTH/ml total volume first and second precursor solutions, most preferably 0.4 mg/ml total volume first and second precursor solutions.

In one preferred embodiment, the kit also contains a spinal fusion device, preferably an interbody fusion cage.

Iv. Methods of Use and Application

The pharmaceutical formulation disclosed herein can be used to make a pharmaceutical product, such as a matrix comprising PTH. In some embodiments, the pharmaceutical product additionally contains an interbody fusion cage.

(A) Method of Making the Pharmaceutical Product

The pharmaceutical formulations described herein are used to manufacture a pharmaceutical product for the stimulation of spinal fusion, preferably, interbody spinal fusion.

The matrix precursor components should be kept separate prior to mixing, to avoid premature polymerization. To prevent premature contact a kit which separates the precursor solutions from each other may be used. Upon mixing under conditions that allow polymerization (crosslinking), the precursor solutions form a PTH three dimensional network. Depending on the precursor components and their concentrations, the gelling time can be tailored to the need.

In one embodiment for forming fibrin matrices, fibrinogen is dissolved in a buffer solution (which may contain additionally aprotinin to increase stability) at physiological pH (in a range from pH 6.5 to 8.0, preferably from pH 7.0 to 7.5) and stored separately from a solution of thrombin in a calcium chloride buffer. The buffer solution for the fibrinogen can be a histidine buffer solution including additionally NaCl or TRIS buffered saline. Both solutions are stored frozen and have to be thawed prior to application.

The fibrinogen and thrombin solutions or the first and second synthetic functionalized precursor solutions are preferably mixed by a two way syringe device, in which mixing occurs by squeezing the contents of both syringes through a mixing chamber and/or needle and/or static mixer. In embodiments where both fibrinogen and thrombin or the synthetic functionalized precursor components are provided in lyophilized form, both are reconstituted prior to use. In case of fibrinogen, a tris or histidine buffer (which may additionally contain aprotinin) is added to the fibrinogen to form a fibrinogen precursor solution. Prior to use, the lyophilized thrombin is dissolved in the calcium chloride solution to form a thrombin precursor solution. Subsequently, the fibrinogen and the thrombin precursor solutions are placed in separate containers, vials or syringe bodies and mixed using a two-way connecting device, such as a two-way syringe.

Optionally, the containers, vials or syringe bodies are bipartite, thus having two chambers separated by an adjustable partition which is perpendicular to the container, vial or syringe body wall. One of the chambers contains the lyophilized precursor components, such as fibrinogen or thrombin, while the other chamber contains an appropriate buffer solution. When the plunger is pressed down, the partition moves and releases the buffer into the chamber to dissolve the lyophilized precursor component, like fibrinogen. After both precursor components are dissolved, both bipartite syringe bodies are attached to a two way connecting device and the contents are mixed by squeezing them through the injection needle attached to the connecting device. Optionally, the connecting device contains a static mixer to improve mixing of the contents.

Cells can also be added to the pharmaceutical composition prior to or at the time of implantation, or even subsequent to implantation, i.e., subsequent to crosslinking of the precursor components.

A granular material, if present, is wetted by injecting sterile water into the syringe in which it is stored. Subsequently, the above-described two-way syringe containing the first and second precursor solutions and the PTH is attached to the syringe containing the wetted granular material. The entire content of the two-way syringe is transferred into the third syringe containing the granular material. The entire content is subsequently injected to the site of the fusion site and is moldable for several minutes.

(B) Method of Using the Pharmaceutical Product

The matrices and matrix forming materials described herein may be administered to a patient in combination with a spinal fusion procedure. The spinal fusion procedure may be performed in the lumbar region, cervical region or thoracic region of the spine.

Patients in need of treatment include individuals with degenerative disc disease, spondylolisthesis (slippage of a vertebra), spinal stenosis, scoliosis, fracture, infection or tumor in the spine. The matrices or matrix forming materials are administered in an effective amount to grow bone in the treatment site and thereby reduce instability and pain in the patient's spine.

When administered locally with an interbody spinal fusion cage and/or with appropriate fixation devices, such as pedical screws or hook rods, the pharmaceutical product is capable of stimulating spinal interbody fusion at every level of the spine. Particularly preferred indications are cervical and lumbar interbody fusions.

In the preferred embodiment, the pharmaceutical product is used in combination with interbody cages that may be formed from a variety of materials (e.g., Poly-Ether-Ether-Ketone (PEEK), CFRP, titanium etc.). Preferably, the interbody cage is made of PEEK or CFRP. The cages are porous and allow bone to grow from the vertebral body through the cage and into the next vertebral body. The cages are typically cylindrical and threaded, although other shapes may be used. In place of threading, the cage may contain teeth along the surfaces to 'bite into' and affix to the end plates.

The supplemented matrix can be formed in the cage prior to its implantation or can be formed directly in situ after the cage has been implanted, inside and outside of the cage. The in situ gelling/formation can occur by mixing matrix material precursor solutions containing the PTH, with the granules (if present) and applying the mixed, preferably crosslinked, composition in the interbody space. Preferably, the crosslinked composition is applied in the interbody cage and then implanted in the prepared disc space. Depending on the indication, operational technique or preference of the surgeon the mixed material can be applied in a still liquid state or in a paste-like consistency. The pharmaceutical formulation or product can also be applied to the disc space prior to insertion of the cage. The formulation or product can be administered inside and outside of the interbody cage, either in a non-crosslinked form, but preferably in a partially crosslinked form (i.e. still moldable) with or without combination with posterior fixation.

In one embodiment, the procedure is performed by approaching the spine through the abdomen, and the cages are placed e.g. in the lumbar region (anterior lumbar interbody fusion or ALIF) or the cervical region (anterior cervical interbody fusion). In another embodiment, the procedure is performed by approaching the spine through the low back such as in posterior lumbar interbody fusion (PLIF) or transforaminal lumbar interbody fusion (TLIF). PLIF achieves spinal fusion in the low back by inserting a bone graft and/or spinal implant (e.g. cage) directly into the disc space. When the surgical approach for this type of procedure is from the back it is called a posterior lumbar interbody fusion (PLIF). TLIF fuses the anterior (front) and posterior (back) columns of the spine through a single posterior approach.

Additionally a posterolateral fusion procedure can be performed, such as to promote spinal stability in patients suffering from conditions such as degenerative disc disease, spondylolisthesis, and spinal stenosis. To that end, vertebrae associated with an impinged or irritated nerve root are permanently connected, or fused, using metal screws and rods that are attached to transverse processes on the vertebrae.

The following examples are included to demonstrate preferred embodiments of the invention. While the compositions and methods have been described in terms of preferred embodiments, it will be apparent to those of skill in the art that variations may be applied to the composition, methods and in the steps or in the sequence of steps of the method described herein without departing from the concept, spirit and scope of the invention. In particular, in all examples $TGplPTH_{1-34}$ was used in a fibrin matrix, and covalently linked thereto. However, different matrix materials, e.g. synthetic matrices, and different PTH peptides, with or without a transglutaminase substrate domain and with or without proteolytic degradation site, may be used. The active agent, i.e. PTH, may be covalently or non-covalently linked to the matrix. Further, the components for the kit of the present invention, the components for forming the pharmaceutical product, and the components of the pharmaceutical formulation, irrespective of whether the formulation is in a spinal fusion cage or not, are the same components as disclosed herein.

EXAMPLES

In the Examples, "$TGplPTH_{1-34}$", "PTH" and "$PTH_{1-34}$" are used synonymously to refer to $TGplPTH_{1-34}$. The concentration of $TGplPTH_{1-34}$ as provided in the Examples in "mg/ml fibrin matrix" or "mg/ml fibrin" refers to the concentration of $TGplPTH_{1-34}$ in the combined precursor solutions used to form the fibrin matrix.

Example 1: Sheep Anterior Cervical Interbody Fusion Model

A fibrin matrix was formed from commercially available TISSEEL VH S/D DUO® (fibrin sealant) or from ARTISS® (fibrin sealant) (Baxter AG, CH-8604 Volketswil/ZH) giving 4 mL fibrin matrix with a composition as listed below. TISSEEL® and ARTISS® are produced from human derived pooled plasma and the contents of active ingredients may vary from lot to lot within predefined ranges.

Test Item:

$TGplPTH_{1-34}$ in fibrin was tested alone or with granular material. PTH in fibrin was prepared using 2 separate syringes, one containing fibrinogen solution and PTH fusion peptide, and the other containing thrombin solution (syringes 1 and 2). PTH in fibrin with granular material was prepared using 3 separate syringes, a two-way syringe containing fibrin precursor solution and PTH fusion peptide (syringes 1 and 2) and two one-way syringes, one containing water and the other containing granules (syringes 3 and 4). Table 2 lists the composition of TISSEEL® or ARTISS® used.

TABLE 2

| Ingredients | Dose in syringe |
|---|---|
| Syringe 1 | |
| Active Component: | |
| $PTH_{1-34}$ fusion peptide ($TGplPTH_{1-34}$) | 0.4-10 mg |
| Clotting Agents | |
| Fibrinogen | 72-110 mg |
| Plasma Fibronectin | 2-9 mg |
| Other Proteins | |
| Aprotinin (Bovine) | 2250-3750 KIE |
| Factor XIII | 1-5 $E^2$ |
| Plasminogen (Human) | 0.04-0.12 mg |
| Human Albumin | 10-20 mg |
| Buffer Components | |
| Niacinamide | 3-9 mg |
| Histidine | 10-25 mg |
| Trisodium Citrate | 4.8-7.9 mg |
| Triton WR 1339 | 0.2-0.4 mg |
| Water for Injection | To 1 mL |
| Syringe 2 | |
| Clotting Agents | |
| Thrombin (Human) | 2.5-6.5 I.U. |
| Buffer Components | |
| Calcium Chloride | 36-44 μmol/L |
| Sodium Chloride | 3.5-5.5 mg |
| Protein (human serum albumin) | 45-55 mg |
|  | 25 mg |
| Water for Injection | To 1 mL |
| Syringe 3 | |
| Water for injection | 1 mL |
| Syringe 4 | |
| Hydroxyapatite/calcium phosphate granules (TCP granules) | 1.75-2 g |

To prepare PTH in fibrin, the fibrin precursor solution of syringe 1 (fibrinogen and PTH suspended in a solution with aprotinin, a serine proteinase inhibitor which helps reduce fibrolysis to retain the integrity of the fibrin matrix) was mixed with the fibrin precursor solution of syringe 2 (thrombin in a calcium chloride solution).

To prepare PTH in fibrin with granular material, first the hydroxyapatite/calcium phosphate granules in syringe 4 was wetted by injection with the water of syringe 3. Then the fibrin precursor solution of syringe 1 was mixed with the fibrin precursor solution of syringe 2 and then, with the granular material.

$TGplPTH_{1-34}$ was formulated into the fibrinogen component to give a final concentration varying from 0 mg/mL (negative control) to 1 mg/mL of the fibrin matrix. The concentrations of $TGplPTH_{1-34}$ used were 0, 0.2, 0.4, 0.7, and 1 mg $TGplPTH_{1-34}$ mg/mL fibrin matrix.

During the gelation process (the process of fibrin matrix formation) $TGplPTH_{1-34}$ becomes crosslinked to the matrix. Fibrin precursor solutions also contain other components of fibrin matrix, such as plasma fibronectin, Factor XIII, plasminogen, and human albumin. When the precursor solutions are in equal volumes, a clotting process occurs to form fibrin, a natural extracellular matrix. The clotting process takes place over several minutes which allows for subsequent manipulation like the simultaneous injection of the mixed solutions into syringe 4, which contain the wetted granules or the application of the product to the site of treatment.

PTH in fibrin was placed in an interbody cage (0.5 ml) prior to implantation. After implantation of the cage, another 3 ml of the product (i.e., PTH in fibrin) was placed around it.

Animals:

A total of 96 Merino female sheep ranging in weight between 51-110 kg (mean: 62.8 kg) and approximately 2 years of age were chosen as experimental animals. The animals were divided into twelve groups (FIG. 1) with autografts as (a) positive and (b) sham operated animals as negative controls. The other groups consisted of the same fibrin matrix with granular material (h-n) or without granular material (c-g) and with different concentrations of TGplPTH$_{1-34}$. Groups were followed for 12 weeks, after which animals were sacrificed at the university owned slaughter house. All animal experiments were conducted according to the German laws of animal protection and welfare and were authorized by the local Ethical Committee and Veterinary Authorities.

Before surgery and for at least 10 days thereafter, the animals were housed inside stalls. While in the stalls, the health status of the animals was evaluated daily for any signs of inflammation or toxicity as represented by pain, infection of the wound, local swellings and/or changed general behavior, for example, food intake, excretion of urine and feces, excitement, apathy etc. After the animals returned to pasture, their health status was evaluated daily by the animal keepers of the LGF-Versuchsstation Nutztierwissenschaften, Lentzealle 75, 14195 Berlin. In the event of any deterioration in health, sheep were returned to the animal facility of the Virchow-Klinikum, Charité-Universitätsmedizin Berlin where they were examined by the veterinarians.

Surgery:

The cervical spine was accessed ventrally. Using an image amplifier, the intervertebral space C3/C4 was identified. After dissection of the ligamentum longitudialis anterior, a discectomy was performed and the adjacent endplates decorticated. Subsequently, the intervertebral space was expanded using a cylindrical bur and an interbody fusion cage (SynCage-C, curved, blue, size 7.0, REF 495.302, SYNTHES®, Synthes GmbH, Eimattstrasse 3, 4436 Oberdorf, Switzerland) pre-filled with the biomaterials (i.e. fibrin with/without granular material), or autograft or left empty (sham control) inserted into the prepared intervertebral space Additional test material was then placed around the cage. The surgical access was closed by using four sutures.

For the positive autograft control group, autogenic bone was harvested from the dorsal part of the left iliac crest through a local incision. The iliac crest was opened using a hammer and chisel. Two cuts at a distance of 3 cm were made and connected on one side, so that this part of the iliac crest could be flapped over like a cover. The cancellous bone was removed using a sharp spoon. The cover was then replaced and fixed into position by a filament (VICRYL® PLUS 1 (Polyglactin synthetic absorbable suture), J&J, Belgium). To close the surgical access, the subcutis was sutured continuously using a resorbable filament (VICRYL® PLUS 3-0, J&J, Belgium). Finally, the skin was closed with a non-resorbable filament (POLENE® (polypropylene suture), 3-0, Ethicon GmbH, Norderstedt, Germany).

Evaluative Procedures:

Animals were sacrificed after 12 weeks and the spine segment containing the C3/C4 intervertebral space was extracted for final analysis. Four different techniques were employed to evaluate the outcome on spinal fusion. The techniques included radiography, non-destructive biomechanical testing, computed-tomography (CT), and histological examinations Radiological Evaluation:

Radiographs were taken before and immediately after surgery, as well as 8 and 12 weeks thereafter (radiography unit: Mobilett Plus, Siemens AG, Fuji CR 24×30, Fuji). Radiographic evaluation was performed by two independent reviewers with respect to three different parameters: disc space height, intervertebral angle and radiographic fusion. All measurements were repeated three times and the final results reviewed by the principal investigator.

Regarding disc space height, anterior, central and posterior intervertebral disc space height of the motion segment C3/C4 was measured on lateral radiographic scans. Subsequently, average intervertebral disc space height was calculated from anterior, central and posterior measurements.

The intervertebral angle was also measured on lateral radiographic scans.

A semi-quantitative score system was developed to evaluate the radiographs. High scores were favourable for bone healing.

Computed Tomography:

After sacrifice, peripheral quantitative computed tomographic (pQCT) scans were performed (Siemens Somatom Plus, Siemens, Erlangen). Axial cuts with a 1 mm slice thickness were made parallel to the intervertebral disc space. Bone mineral densities (BMD) were determined as described by Kandziora and Pflugmacher (Kandziora, et al., *Spine*, 26(9):1028-37 (2001) and Kandziora, et al., *Spine*, 29(17):1845-55 (2004) (discussion 1856). BMD measurements were calibrated with a 6-point bone mineral density phantom.

Four distinct and separate regions of interest were identified inside the cage and an individual measurement of BMD was made for each region. The chosen regions were identical in all samples to ensure comparability of the results. For defining the regions, the holes present in the spinal fusion cages were taken as landmarks. Additionally, four regions in the vertebral bodies C3 and C4 were measured.

Measurements were performed using specific scanner software (Sienet Magic View VA 30A, Siemens, Inc., Erlangen, Germany). All parameters were evaluated by three independent reviewers.

Nondestructive Biomechanical Testing:

After the animals were sacrificed, the biomechanical properties of the treated segments were evaluated by non-destructive mechanical testing. Pure bending moments were applied to the motion segment C3/C4 using a system of cables and pulleys to induce flexion and extension, left and right lateral bending and left and right axial rotation. Tension was applied to the cables with a uniaxial testing machine (Zwick 1456, Zwick GmbH, Ulm, Germany) (Kandziora, et al., *Spine*, 26(9):1028-37 (2001))

Three-dimensional displacement of each motion segment was measured using an optical measurements system (Qualysis, Inc., Sävebalden, Sweden). Two triangular markers with three diodes (Qualysis, Inc., Sävebalden, Sweden) were attached to the C3 and C4 vertebral bodies. Marker positions were detected with two cameras and recorded using a computer-controlled system to study micromotions (PC-Reflex; Qualysis, Inc., Sävebalden, Sweden). Angular displacement of C3 in relation to C4 was calculated by using custom designed software.

Vertebral bodies were embedded in a two component plastic (BERACRYL POWDER® (methyl metacrylate) Bauer Handels GmbH Waberg, Adetswil, Switzerland)) to ensure proper fixation and also to ensure that the lower extremity of the segment was attached rigidly to the base of the testing apparatus. The weight of the apical fixation device resulted in an axial preload of 25 N, corresponding approximately to the weight of a sheep head. The samples were kept wet during the whole testing procedure. Moments were applied in increments of 1 Nm per second up to a maximum of 6 Nm. Specimens were first preconditioned with three cycles. Data was then acquired during the application of the fourth cycle. The range of motion (ROM), the neutral and elastic zone, as well as the stiffness values were determined from the corresponding torque-angular displacement curves.

Histology.

After biomechanical testing, the vertebral C3/4 motion segments were subjected to histological analysis of nondecalcified, parasagittal sections using different stains to assess the effects of the biomaterials. Histomorphological and histomorphometric analysis, as well as a determination of the histological fusion was performed.

First, the segments were fixed for one day in 10% normal buffered formaldehyde. Then the segments were cut sagitally and parasagitally in 8 slices of 4 mm and subsequently fixed for a further 7 days in 10% normal buffered formaldehyde. Afterwards, the residual parts of the cages were removed and the slices were dehydrated in ascending concentrations of ethanol. After embedding, either in paraffin or in methyl methacrylate, longitudinal sections of 6 μm were cut in the sagittal plane (Leica SM 2500S Microtome) and the following coloration techniques used:

Safranin orange/von Kossa
Movat pentachrom
Methyl green/van Gieson

Bone and connective tissue were determined from Safranin orange/von Kossa stains, cartilage, from Movat pentachrom stains and granules, from Methyl green/van Gieson stains.

The histological fusion score within the cage was evaluated based on one central slide by two independent reviewers on the Safranin orange/von Kossa stained slices using a three scale scoring system.

Sections stained by Safranin orange/von Kossa, Methyl green/van Gieson and Movat pentachrom were used for histomorphometry. Parameters were measured using a Leica DM-RB microscope and an image analysis system (Zeiss KS 400, Zeiss GmbH, Germany).

Region(s) of interest (ROI) were first defined. As a first region, an overall ROI was defined by the width of the original intervertebral disc and a height of 35 mm. Inside this ROI, 5 different sub regions were defined. The cage ROI was a rectangle of 7 mm in height and 12 mm in width at the location of the cage. Adjacent to the cage ROI, a dorsal and ventral ROI were defined ranging from the cage to the dorsal or ventral end of the vertebra, respectively. Furthermore, a cranial and caudal ROI were defined to include 5 mm of the cranial (C3) or the caudal (C4) vertebra adjacent to the cage.

The following structural indices were calculated in the ROI:

1. bone area/total area (total area being the surface within the cage in the specific histological slice)
2. cartilage area/total area
3. area of connective tissue/total area
4. area of granules/total area (only for groups treated with the biomaterial containing granular material)

Histomorphology.

Sections stained by Safranin orange/von Kossa, Movat pentachrom and for the Bone Graft Substitute groups additionally Methyl green/van Giesson were used for histomorphology.

Histomorphological analysis was performed in the five ROI to determine ventral fusion, presence of woven bone, hyaline cartilage, potential foreign body reaction, vascularization, osteolysis and the occurrence of osteoclasts and osteoblasts. Two separate reviewers performed the evaluation of the different groups: one evaluated the autograft and the biomaterial without granules; the other evaluated the sham and the biomaterial with granules.

Results

Bone Mineral Density (BMD) and Radiographic Parameters:

A low level of bone formation was observed in empty cages (i.e. sham control) while significant bone formation was observed with autograft.

Treatment with the biomaterial without granules showed clear bone formation within the spinal fusion cage and thus, promotion of spinal fusion. Dependent on the analytical technique used, a dose dependency was observed, with best results obtained with $TGplPTH_{1-34}$ at 0.2 and 0.4 mg/mL fibrin. On measuring BMD similar or better results than those obtained with autograft were obtained (FIG. 1). The biomaterials without granules also performed similarly or better than autograft when radiographic parameters were determined. Radiographic parameters look at the presence of continuous bone between the two vertebras, while maintenance of disc space is a measure of the evolution of the distance between the two vertebrae. After fusion occurs the distance between the two vertebra remain stable The biomaterial with granules showed similar results in the radiological parameters (i.e., disc space height, intervertebral angle and radiographic fusion) as the autograft; however, granules were still present at sacrifice in animals, which may have led to an overestimation of the radiographic fusion score and BMD for these groups. For these animals the BMD was higher (better) than autograft.

Histological Analysis

Histomorphometric analysis demonstrated that all the groups treated with the biomaterial without granules showed an increase in percentage of bone compared with the sham operated animals. Cartilage didn't show a clear trend, while connective tissue tended to be lower in the treatments compared to empty, except for the groups treated with the granules where it was higher than in the empty group (The percentage of bone is calculated by dividing the area of bone by the total area of the cage in a given histological slice; the same calculation principle was applied for cartilage and connective tissue). Moreover, the biomaterial containing 0.2 mg of TGplPTH1-34/mL fibrin presented comparable results to autografts in the percentage of bone, cartilage and connective tissue.

The biomaterial with granules presented a low percentage of bone in comparison to autograft. The amount of cartilage was variable, while the connective tissue was always high compared to autograft and even to sham Best results were obtained with a concentration of 0.2 mg of TGplPTH1-34/mL fibrin. The histomophometric analyses was negatively influenced by the radioopacity of the granules.

Biomechanical Testing

The improved results in the group treated with TGplPTH$_{1-34}$ compared to the control groups (sham control and autograft) demonstrated that the presence of clinically relevant doses of TGplPTH$_{1-34}$ in the biomaterials of the present invention can lead to a strong improvement in healing. The faster healing, and improved bone formation are relevant characteristics to justify application of the pharmaceutical products disclosed herein in spinal fusion procedures. Furthermore, when the results of the radiological evaluation, BMD and histological fusion are evaluated, it can be seen that doses between 0.2 mg/mL to 0.7 mg/mL TGplPTH$_{1-34}$ fibrin matrix is the most preferred concentration range.

Example 2: Sheep Transforaminal Lumbar Interbody Fusion Model

As in example 1, PTH (i.e. TGplPTH$_{1-34}$) was tested alone or with granular material. The same materials were used as in example 1, and the preparation of the product followed the same protocol as for example 1, but in this study the concentrations of TGplPTH$_{1-34}$ ranged from 0.2 mg/mL to 0.7 mg/mL of the fibrin matrix. The treatment was placed only inside the interbody cage. No additional test material was placed around the cage, as in example 1.

Animals:

A total of 28 Crossbred Suffolk Sheep (Castrated Weathers) with an average weight of 57 kg and age ranging from 3 to 6 years of age were chosen as experimental animals. The animals were divided into 7 groups. One group (the positive control group) was treated with autograft and the remaining groups were treated with a fibrin matrix with or without granular material, containing different concentrations of TGplPTH$_{1-34}$. Groups were followed for 16 weeks, after which the animals were sacrificed. Animal care and use was conducted in accordance with federal regulations as outlined in the Animal Welfare Act. Surgery, perioperative care, housing, sanitation practices, husbandry, and veterinary care followed the recommendations of the *NIH Guide for the Care and Use of Laboratory Animals* (HHS, NIH Pub. No. 85-23, 1985). Animal care personnel were qualified, through training and experience, to perform required duties.

All animals received physical examinations by a veterinarian within two weeks prior to surgery to ensure normal health status. Any animals determined pre-operatively or during surgery to have an osseous abnormality problem (e.g. tumor, osteomyelitis) or other disqualifying factor were excluded from the study. Animals were provided a 6'×10' pen pre-operatively and for the entire post-operative period. An isolation pen was available for special procedures and treatments, if necessary.

Prior to surgery, all animals were placed under food restriction (NPO) for forty-eight hours and housed in the isolation pen care facility. All animals were examined daily by the study director for the first ten days post-operatively for mortality, wound site healing, ambulatory function, clinical signs of ill health, and behavioral (social) changes. After ten days post-operatively, these observations were performed and recorded by the animal care personnel technicians. Particular attention was given to the surgical site with an emphasis on wound healing and signs of infection, if any. Animals judged to be abnormal by the facility staff were referred to and examined by the study director and a veterinarian daily. Observations and serious adverse events were recorded on the case report forms and commented on with regard to diagnosis, severity, treatment, and outcome.

Surgery:

Following intravenous administration of anesthetic medications and induction of general anesthesia, the anterolateral lumbar region and iliac crest was aseptically prepared. Following lateral recumbency positioning of the animal, surgical exposure consisted of a ten to fifteen centimeter incision beginning at the iliac crest and extending along the palpable borders of the lumbar transverse processes along the anatomic right. Detachment of the external abdominal oblique from the transverse processes was performed, followed by soft tissue dissection to permit retroperitoneal exposure of the psoas muscle. Using a periosteal elevator and electrocautery, the anterolateral aspects of the L2-L3 and L4-L5 vertebral bodies and intervertebral discs were exposed. The ventral nerve roots crossing over the disc surface were transected, followed by discectomy and burr removal of the vertebral endplates to a dimension of approximately 24 mm depth×11 mm wide×11 mm height at both operative levels. Caspar pin segmental distraction was performed at each operative level to assist in endplate removal and interspace preparation. Once prepared, the TETRIS™ PEEK (Poly-Ether-Ether-Ketone) cage (spinal implant) (Signus Medical, LLC) was filled with 1.6 mL of TGplPTH$_{1-34}$ in fibrin with or without granular material at the concentrations discussed above according to the treatment randomization schedule and securely implanted within the disc space. 100% morselized cancellous iliac autograft served as operative control. Each animal received the same treatment at both operative levels to avoid cross contamination of different dosages. Treatments were performed according to a pre-defined randomization table, strictly according to the manufacturer's recommendations for device implantation. For wound closure, the muscle, subcutaneous layer, and skin were approximated with running and interrupted 1-0 VICRYL® (polyglycolic acid) sutures.

Under the same anesthesia, the animal was re-positioned prone, aseptically prepared and draped in sterile fashion. An initial skin incision was made in the dorsal mid-line of the low back centered over the L2-S1 levels. Blunt dissection using a Cobb elevator and electrocautery, when necessary, was performed in the sagittal plane along the neural arch-permitting exposure of the L2-L3 and L4-L5 facets and transverse processes. After fluoroscopic verification of the previously implanted cage, the two operative levels (L2-L3 and L4-L5) were instrumented using transpedicular screw and rod fixation (S4® Spinal System—Aesculap Spine USA, Inc.). For wound closures, the muscle, subcutaneous layer, and skin were approximated with running and interrupted 1-0 VICRYL® (polyglycolic acid) sutures and the skin closed with staples. Data on anesthesia type and duration, surgery duration, estimated blood loss, treatment assignment, complications, antibiotics and analgesics were recorded at the time of the surgical procedure.

Evaluative Procedures:

Animals were humanely sacrificed after 16 weeks. The spinal column of each animal was carefully removed and immediately placed in double wrapped plastic specimen bags and frozen at −25° C. for subsequent radiographic, biomechanical and histologic evaluation of the operative motion segments.

Radiological Evaluation:

Anteroposterior and lateral fluoroscopic images of the lumbar region were obtained intra- and post-operatively to verify implant placement. Plain films were obtained post-operatively and at animal sacrifice to evaluate implant location and endplate radiolucencies. For each operative segment, computed tomography images were obtained between the cephalad and caudal pedicle levels of the arthrodesed segments in one-millimeter-thick slice intervals (Dedicated Imaging, Inc., Baltimore, Md.). CT images were used to qualitatively assess the success of interbody fusion and location of the graft materials within the treatment level, incidence of spinal stenosis and/or ectopic calcification anterior or lateral to the implanted cage. Arthrodesis sites were graded as fusion, partial or non-union by four individuals blinded to the treatment group. Fusion was defined as "yes" if at least two sagittal slices on the CT images demonstrated evidence of contiguous bone from endplate to endplate without signs of radiolucencies, while partial union was based on one sagittal image containing contiguous bone. Anteroposterior and lateral plain films of the lumbar region were obtained intra- and post-operatively to verify implant placement.

Non Destructive Biomechanical Testing:

In preparation for biomechanical testing, the lumbar motion segments were thawed to room temperature and cleaned of all residual musculature with care taken to preserve all ligamentous attachments and operative motion site integrity. The cephalad and caudal ends of each specimen were secured in rectangular containers using eight compression screws. A total of three Plexiglas motion detection markers were placed on the specimen: Marker 1—superior element, Marker 2—inferior element and Marker 3—base. Each marker was equipped with three non-colinear light emitting diodes designed for detection by an optoelectronic motion measurement system (3020 OptoTrak System). To determine the multidirectional flexibility properties, six pure, unconstrained moments: flexion and extension (±4 Nm X-axis), left and right lateral bending (±4 Nm Z-axis) and left and right torsion (±4 Nm Y-axis) were applied to the superior end of the vertically oriented specimen while the caudal portion of the specimen remained fixed to a testing platform. A maximum applied moment of ±4 Nm was used for each loading mode and applied at a ramp rate of three degrees/second using a six degree of freedom spine simulator (6DOF-SS). A total of three load/unload cycles were performed for each motion, with data analysis based on the final cycle. For the six main motions—corresponding to the moments applied—the operative level vertebral rotations (degrees) were quantified in terms of peak range of motion (ROM). To prevent desiccation during assessment, specimens were moistened with 0.9% NaCl sterile irrigation solution.

Destructive Biomechanical Testing:

A destructive mechanical test was undertaken to quantify the structural material properties of the tissue within the PEEK cage. One L4-L5 operative motion segment was assessed for each treatment group. The operative motion segments were transversely sectioned directly along the superior and inferior edges of the PEEK cage using a Beuhler Isomet Cutting system and diamond wafering blade. Two parallel surfaces were obtained using this technique. The explanted cage was then mounted on the testing platform of an MTS 858 Bionix Test system. Indentation compression tests were performed using a 3 mm diameter punch indenter at a displacement rate of 0.2 mm per second to a depth of 4 mm. Three tests were performed on each side of the superior and inferior surfaces with calculation of peak failure load (Newtons) for each test site from the load-displacement curves (n=6 indentation sites per cage). A total of eight cages were tested (one per group) and compared to an intact non-operative control. The operative specimens were subsequently processed using undecalcified technique to characterize the histological tissues present at each test site and correlate these findings with the observed mechanical properties. These mechanical testing methodologies have been previously reported: (Grant J P et al., $Spine$, 26 (8):889-896, (Apr. 15, 2001); and (Oxland T R et al., $Spine$ 28(8):771-777(Apr. 15, 2003).

Histopathologic and Histomorphometric Evaluation:

Following biomechanical analysis, the operative lumbar motion segments not included in the destructive mechanical testing were sagittally sectioned along the geometric centerline of the implanted device using a Beuhler Isomet saw. The tested cage samples were also processed using undecalcified technique but sectioned coronally. Histologic preparation of all samples included dehydration in 100% ethanol, staining using the Villanueva Osteochrome Bone Stain, undecalcified solution processing and embedding in polymethyl-methacrylate (PMMA). Using the EXAKT Microgrinding Device, the embedded specimens were cut to 300 to 600 μm in thickness, ground and polished to 130 μm. Microradiographs were obtained of the slide-mounted specimens using Faxitron radiography. The slides were placed twelve inches from the beam and exposed for two minutes, using a technique of 34 kVp and 2 mA while in direct contact with the single emulsion high-resolution graphics arts film. The high-resolution microradiographs and light microradiographs were used for fusion assessment by two reviewers blinded to the treatment groups. Fusion was defined as contiguous bone from endplate to endplate without evidence of interruptive radiolucencies within the cage. Partial union was evidenced by one contiguous strand of bone bridging the endplates, while non-union was a continuous radiolucent gap spanning the cage. Histomorphometric quantification of seven different parameters within the confines of the PEEK Cage included the following: Region of Interest (ROI) ($mm^2$), PEEK Implant Area ($mm^2$), Granules Area ($mm^2$), Bone Area ($mm^2$), Marrow Area ($mm^2$), Net Tissue Area ($mm^2$) and Trabecular Bone/Net Tissue Area (%). The net tissue area represents the region of interest minus the PEEK area. The PEEK cage samples included in the destructive indentation testing were evaluated using plain light microscopy to characterize tissues present.

For all specimens, the spinal cord (n=2 per specimen) and local tissue overlying the implant sites (n=2 per specimen) were resected, sectioned and prepared by a veterinarian pathologist. The specimens were fixed in a 10% formalin solution and subjected to routine paraffin processing. Slide preparation was performed by the University of Maryland Biotechnology Institute (UMBI) Histology Laboratory (UMBI, Baltimore, Md.). Using thin-sectioning microtomy, the paraffin embedded sections were cut (3-5 μm in thickness), slides were mounted and stained using standard Hematoxylin and Eosin (H&E) and special Macrophage Stain (HAM-56). Pathological assessment for all tissues included comments on tissue architecture, presence of wear debris, incidence of mineralization in local tissue/spinal cord histology, osteolysis as well as any signs of foreign body giant cell/granulomas inflammatory reactions, degenerative changes or autolysis.

Results

No toxicity was observed during the treatment period with any of the $TGplPTH_{1-34}$ doses or formulations used.

Histopathologic review of all treatment groups combined indicates no evidence of foreign body/inflammatory reaction or significant pathological changes. Many treatments contained interpositional pockets of cartilaginous/collagenous tissue, which is actively remodeling. In almost all cases, the trabecular bone within the PEEK cages was densely woven and sclerotic in most regions, containing normal osteocyte distribution and osteoid seam widths. Overall, there were no signs of osseous pathology due to any of the formulations or dosages of $TGplPTH_{1-34}$ utilized in this investigation. All histological specimens could be characterized as unremarkable and undergoing a normal healing process, without evidence of giant cell reaction/inflammatory response or other significant histopathological changes.

Figure 2:
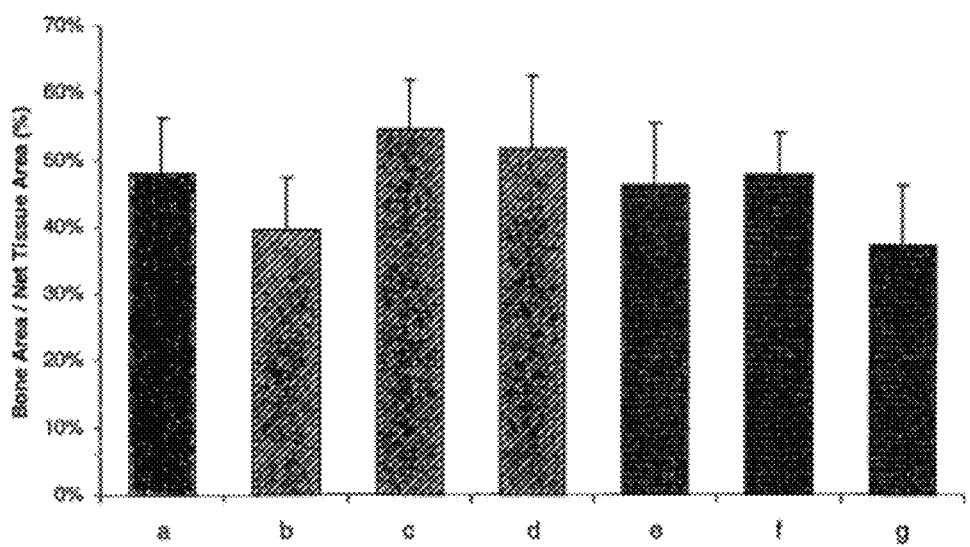
FIG. 2 is a bar graph showing histomorphometry results (bone area/tissue area (%)) obtained with different PTH formulations in a sheep transforaminal lumbar interbody fusion model. Autograft (a); 0.2 mg $TGplPTH_{1-34}$/mL fibrin matrix (b); 0.4 mg $TGplPTH_{1-34}$/mL fibrin matrix (c); 0.7 mg $TGplPTH_{1-34}$/mL fibrin matrix (d); 0.2 mg $TGplPTH_{1-34}$/mL fibrin matrix+granular material (e); 0.4 mg $TGplPTH_{1-34}$/mL fibrin matrix+granular material (f); and 0.7 mg $TGplPTH_{1-34}$/mL fibrin matrix+granular material (g).

Plain film radiographic analysis demonstrated no evidence of implant migration. Sagittal and coronal CT images showed successful fusions in the autograft and in the treatment with the biomaterials. For the biomaterial without granules, the best results were obtained at a concentration of TGplPTH1-34 between 0.4 and 0.7 mg/ml (eight out of eight animals and six out of eight animals respectively were scored as fused, versus four out of eight animals fused in the lower dose (0.2 mg/ml)), while for the biomaterial with granules best results were obtained at a concentration of TGplPTH of 0.2 mg/ml (seven out of eight animals fused versus five out of eight with 0.4 or 0.7 mg/mL). Histological fusion scoring confirmed the radiographic outcome showing 100% of samples fused in the autograft and in the biomaterial without granules with TGplPTH1-34 at 0.4 mg/ml; 85% of fusion in the groups treated with the biomaterial with granules with TGplPTH1-34 at 0.2, 0.4 and 0.7 mg/ml; 71% and 43% of fusion in the group treated the biomaterial without granules with TGplPTH1-34 at 0.7 and 0.2 mg/ml, respectively In the histomorphometric quantification, the percentage of bone area in the cage was highest for the 0.4 mg/mL $TGplPTH_{1-34}$ in the biomaterial without granules followed by the 0.7 mg/mL group and the autograft group. The data is shown in FIG. 2.

Biomechanical testing was conducted to determine the multi-directional flexibility properties of the lumbar segments, where better stability is indicated by a lower range of motion. Results showed that $TGplPTH_{1-34}$ at 0.4 mg/mL in the biomaterial without granules and all $TGplPTH_{1-34}$ concentrations in the biomaterial with granules provided mechanical stability comparable to autograft. The data are not provided. In Example 2 the time point was longer than in Example 1, and for this reason the fusion observed are complete and biomechanically stable. In general, the granules confer structural support and may contribute to mechanical stabilization.

The results obtained in the group treated with selected concentration of $TGplPTH_{1-34}$ in the biomaterials are comparable or better than the positive control group demonstrating that the presence of clinically relevant doses of $TGplPTH_{1-34}$ in the biomaterials as disclosed herein can lead to an effective bone graft substitute for spinal fusion. Furthermore, when the results of the radiological, biomechanical and histological evaluation are considered, it can be seen that $TGplPTH_{1-34}$ at doses between 0.4 mg/mL to 0.7 mg/mL fibrin matrix is the preferred concentration range in the biomaterial without granules and $TGplPTH_{1-34}$ at doses between 0.2 mg/mL to 0.7 mg/mL fibrin matrix is the preferred concentration range when granules are included.

Example 3: Baboon Anterior Lumbar Interbody Fusion Model

The same materials were used as in the previous Examples (except for granular material, which was not present in the $TGplPTH_{1-34}$-fibrin composition of this Example 3).

Test Item:

$TGplPTH_{1-34}$ was added into the fibrinogen component to give a final concentration of 0.4 mg/mL of the fibrin matrix.

Animals:

A total of three (3) olive or yellow baboons of approximate weight of 30 kg of each animal and 8 to 11 years of age were chosen as experimental animals. The baboons were subjected to a L4/L5 and L6/L7 discectomy and fusion using a radiolucent vertebral cage. In each animal one level contained a total volume of 0.7 mL of autologous bone graft inside the cage (positive control), whereas the other level contained the same volume of 0.4 mg of $TGplPTH_{1-34}$ per mL of fibrin. The two interventional segmental levels were block-randomized to the autograft control and the treatment group. The animals were followed for 6 months, after which animals were sacrificed. All animal experiments were conducted at the Southwest Foundation for Biomedical Research (SFBR), 7620 NW Loop 410, San Antonio, Tex. 78227, USA, according to the laws of animal protection and welfare ("Animal Welfare Act" and "Guide for the Care and Use of Laboratory Animals"). The experiment was authorized by the Institutional Animal Care and Use Committee (IACUC).

Before and after surgery, animals were checked regularly for their general health status.

Surgery:

The animals were placed in a supine position. Surgical exposure consisted of a 10-15 cm incision in the left lateral abdominal wall, followed by soft tissue dissection to allow retroperitoneal exposure of the anterior lumbar spine. Blunt dissection using a Cobb elevator and electrocautery was performed as needed, to expose the anterior aspects of the L4/L5 and the L6/L7 vertebral bodies with interposed intervertebral discs. Intra-operative radiography was used to verify the operative levels. The aorta and vena cava overlying the anterior lumbar spine were gently retracted and two non-contiguous disc sites (L4/L5 and L6/L7) were prepared in the lumbar spine, for insertion of the implant spacers. For this purpose, a rectangular window approximately 15 millimeter (mm) wide, centered and extending from the caudal to the cranial endplate rim was cut into the discs. The disc material was gradually removed using small rongeurs and curettes and until the endplates were bleeding from the whole cross-sectional area. A PEEK cage, properly sized to find a tight fit, was filled with either autologous bone or $TGplPTH_{1-34}$ in fibrin, before insertion into the prepared intervertebral disc space. For the autograft treatment, cortico-cancellous bone graft chips were harvested using a curved chisel and a hammer along the inside of the left anterior ileum wing. Care was taken not to violate the outer cortical shell of the wing. The chips were then further cut with a bone rongeur into smaller pieces that were used to densely pack the inside of the cage. For wound closure, the muscles and fascia were approximated using 1-0 VICRYL® and the skin closed with 2-0 VICRYL® sutures. The implant position was documented directly after surgery by radiographs in antero-posterior and lateral view.

Evaluative Procedures:

Radiological analyses were performed every 4 weeks until sacrifice. During the follow up time, various fluorescent compounds were administered in order to allow the monitoring of calcium apposition over time. Animals were sacrificed after 24 weeks and the vertebral segments L4/L5 and L6/L7 were harvested for final analysis. Three different techniques were employed to evaluate the surgical results. These included radiography/microradiography, micro computed tomography (μCT) and histological examinations.

Radiological Evaluation:

Radiographs were taken in antero-posterior and lateral projections before and directly after surgery, as well as every four weeks thereafter up to 24 weeks following surgery. Films were used to qualitatively assess the evolution and success of interbody fusion through the study, as well as to identify cage migration and reduction of the intervertebral space. Radiographic evaluation was performed by two independent reviewers blinded to the treatment group following a semi-quantitative scoring system from 0 to 3 for the fusion, and from 0 to 2 for cage displacement and disruption of vertebral space.

Micro Computed Tomography:

μCT analysis was performed with respect to the bone present in the spinal fusion cage. An algorithm was used to create a mask representing the inner volume of the cage. First, a region of interest equal to the inner shape of the spinal fusion cage was defined. Within this region of interest, bone volume was analyzed (bone volume/total volume in the cage) (BV/TV). Histology: Histological analysis was performed qualitatively and semi quantitatively. For each level, three thick histological sections were prepared for the mid-sagittal plane, as well as for both para-sagittal planes with an offset of about 4 mm. After flattening by weights for two days, microradiographs were taken (Faxitron), then ground to a thickness of 30-40 micrometer (μm) and stained with Toluidine blue. Qualitative analysis of histological sections was conducted focusing on the fusion within the cage, cage displacement, disc material/cartilage, and callus formation (scoring 0 to 3). From each level two histological thin sections were prepared to semi quantitatively score the presence of osteoblast, osteoclast, foreign body cells, lymphocytes, macrophages and plasma cells. Histologically thin sections were prepared and stained with Toluidine blue and Von Kossa/McNeal Tetrachrome counterstain.

Histomorphometry:

Quantitative histology was performed blinded to the experimental groups. First, the pictures was coloured for different features (e.g. fibrous tissue, old bone, new bone etc.) using Adobe Photoshop® (computer program). Histomorphometry was performed by a standardized and automated procedure and quantified using a Leica® microscope. After taking a picture of the Toluidine Blue colored histological slice, bone, cartilage and connective tissue were detected with Photoshop® based on their color intensity. The area of the bone and the total area inside of the cage were quantified with Photoshop®. The ratio between the two was expressed as the % of bone within the cage.

Results

No safety issues were seen with the use of the material and in particular no hypercalcemia was seen in the blood analysis.

Radiographic, histological and μCT analysis demonstrated a reduction of the intervertebral space in most levels, which may be secondary to the surgical procedure. An anterior migration of the PEEK cage was also observed in some levels, which could have created the loss of some material.

Radiographic fusion showed complete bridging or clear bridging with a small intervertebral gap in all animals in the treatment groups TGplPTH$_{1-34}$ in fibrin, with a similar fusion trend than autograft internal control.

Figure 3:
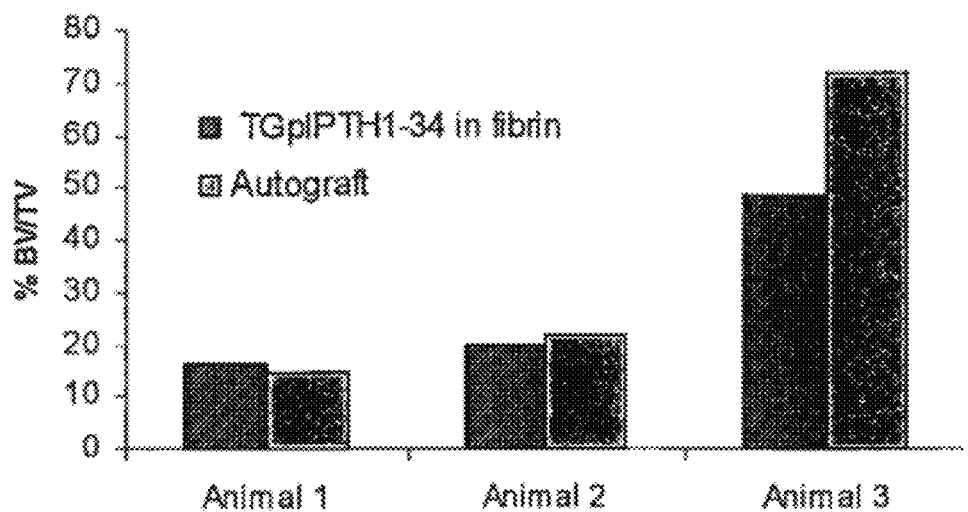
FIG. 3 is a bar graph showing the micro computed tomography (μCT) analysis comparing bone volume/total volume (BV/TV) obtained with 0.4 mg of $TGplPTH_{1-34}$/mL of fibrin matrix (left bar) and autograft (right bar) in a baboon anterior lumbar interbody fusion model.
Figure 4:
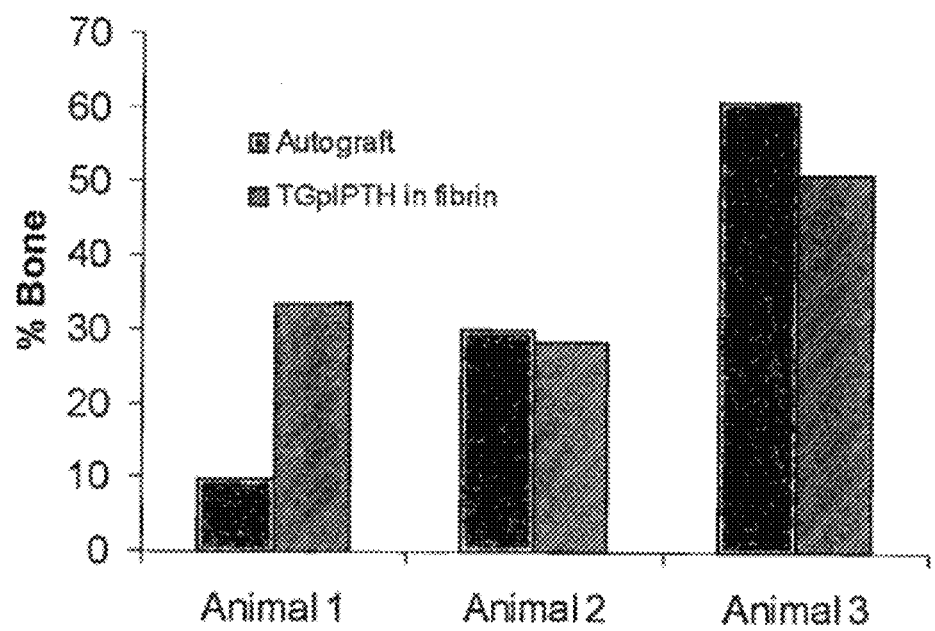
FIG. 4 is a bar graph histomorphometry comparing the percent bone obtained with 0.4 mg of $TGplPTH_{1-34}$/mL of fibrin matrix (right bar) and autograft (left bar) in the baboon anterior lumbar interbody fusion model. The % bone is defined as the bone area in the cage/cage area×100.

Histological fusion scoring was performed based on the percentage of bony bridging within the cage. In general a low level of fusion was observed with only bony bridging in one level treated with autograft. Looking at the bone deposition within the cage overtime, autograft and TGplPTH$_{1-34}$ in fibrin showed bone formation at 8 and 13 weeks, but not afterwards.

μCT analysis for percentage of bone formation within the cage (FIG. 3) and histomorphometry results (FIG. 4) showed consistent results. The level of bone formation was variable among animals, but comparable between the treated and the control group.

Histomorphological analysis showed no major differences in terms of cell presence (osteoblast, osteoclast, foreign body cells, lymphocytes, macrophages and plasma cells) between control autograft and treatment group. This study showed that TGplPTH$_{1-34}$ in fibrin is able to promote spinal fusion in a nonhuman primate model with efficacy and timing comparable to ileac crest autograft.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A spinal fusion method for treatment of a human patient in need thereof, comprising
administering to the patient at a site between two adjacent vertebrae in need of spinal fusion a pharmaceutical composition capable of forming under physiological conditions a bone graft substitute,
wherein the pharmaceutical composition comprises one or more matrix forming materials and parathyroid hormone (PTH), wherein the composition does not contain any additional added peptide or protein bioactive factor with bone forming properties,
wherein during or after administration, the pharmaceutical composition forms a bone graft substitute at the site,
wherein the bone graft substitute comprises a matrix and the PTH, and does not contain any additional added peptide or protein bioactive factor with bone forming properties,
and
wherein the bone graft substitute locally delivers the PTH to the site in an effective amount to achieve bone formation between the vertebrae.

2. The method of claim 1 wherein the one or more matrix forming materials comprise:
(i) a first matrix precursor component,
(ii) a second matrix precursor component,
and wherein the first and the second matrix precursor components interact with each other in order to form the matrix during or after their administration to the site.

3. The method of claim 2, wherein the first matrix precursor component comprises fibrinogen and the second matrix precursor component comprises thrombin, and the composition further comprises a calcium source.

4. The method of claim 1, wherein the PTH is selected from the group consisting of $PTH_{1-84}$, $PTH_{1-38}$, $PTH_{1-34}$, $PTH_{1-31}$, and $PTH_{1-25}$.

5. The method of claim 1, wherein the PTH is a PTH fusion peptide comprising at least two domains wherein the first domain comprises PTH and the second domain comprises a crosslinkable substrate domain.

6. The method of claim 5, wherein the PTH fusion peptide further comprises an enzymatic or hydrolytic degradation site between the first and the second domains.

7. The method of claim 6, wherein the degradation site is a substrate for plasmin, and wherein the PTH fusion peptide is $TGpl\text{-}PTH_{1-34}$.

8. The method of claim 1, wherein the spinal fusion is selected from the group consisting of cervical and lumbar interbody fusions.

9. The method of claim 2, wherein the composition further comprises a granular material, wherein the granular material is a biodegradable ceramic compound selected from the group consisting of hydroxyapatite, calcium phosphate and calcium sulphate.

10. The method of claim 2, wherein the first matrix precursor component comprises strong nucleophilic groups or bonds, and the second matrix material precursor component comprises strong electrophilic groups or bonds.

11. The method of claim 1, wherein the matrix is selected from the group consisting of glycoproteins, polysaccharides, glycosaminoglycans, and ceramics and combinations thereof.

12. The method of claim 1, further comprising placing an interbody spinal fusion cage between the vertebrae at the site in need of fusion.

13. The method of claim 12, wherein the pharmaceutical composition is placed in and around the fusion cage.

14. A spinal fusion method for treatment of a human patient in need thereof, comprising
administering to the patient at a site between two adjacent vertebrae in need of spinal fusion a bone graft substitute,
wherein the bone graft substitute comprises a matrix and parathyroid hormone (PTH), and does not contain any additional added peptide or protein bioactive factor with bone forming properties, and
wherein the bone graft substitute locally delivers the PTH to the site in an effective amount to achieve bone formation between the vertebrae.

* * * * *